(12) United States Patent
Meretzki

(10) Patent No.: US 9,987,394 B2
(45) Date of Patent: Jun. 5, 2018

(54) BONE-LIKE PROSTHETIC IMPLANTS

(76) Inventor: Shai Meretzki, Haifa (IL)

( * ) Notice: Subject to any disclaimer, the term of this patent is extended or adjusted under 35 U.S.C. 154(b) by 311 days.

(21) Appl. No.: 12/937,273

(22) PCT Filed: Apr. 7, 2009

(86) PCT No.: PCT/IL2009/000395
§ 371 (c)(1),
(2), (4) Date: Feb. 28, 2011

(87) PCT Pub. No.: WO2009/125402
PCT Pub. Date: Oct. 15, 2009

(65) Prior Publication Data
US 2012/0003185 A1 Jan. 5, 2012

Related U.S. Application Data

(60) Provisional application No. 61/071,064, filed on Apr. 10, 2008, provisional application No. 61/136,557, filed on Sep. 15, 2008.

(51) Int. Cl.
*A61L 27/38* (2006.01)

(52) U.S. Cl.
CPC ....... *A61L 27/3843* (2013.01); *A61L 27/3804* (2013.01); *A61L 27/3886* (2013.01); *A61L 2430/02* (2013.01)

(58) Field of Classification Search
CPC ....... A61K 35/32; A61K 35/12; A61K 35/28; C12N 5/0643; C12N 5/0663; C12N 2502/1142; A61L 2430/02; A61L 27/12; A61L 27/3847; A61L 27/3804; A61L 27/3886; A61L 27/3843
USPC ....... 424/93.7, 422, 549, 93.1; 435/325, 373
See application file for complete search history.

(56) References Cited

U.S. PATENT DOCUMENTS

| | | | |
|---|---|---|---|
| 4,186,448 A | 2/1980 | Brekke | |
| 5,133,755 A | 7/1992 | Brekke | |
| 5,514,378 A | 5/1996 | Mikos | |
| 5,522,895 A | 6/1996 | Mikos | |
| 5,607,474 A | 3/1997 | Athanasiou | |
| 5,677,355 A | 10/1997 | Shalaby | |
| 5,686,091 A | 11/1997 | Leong | |
| 5,716,413 A | 2/1998 | Walter | |
| 5,716,616 A | 2/1998 | Prockop | |
| 5,755,792 A | 5/1998 | Brekke | |
| 5,769,899 A | 6/1998 | Schwartz | |
| 5,770,193 A | 6/1998 | Vacanti | |
| 5,824,084 A | 10/1998 | Muschler | |
| 6,049,026 A | 4/2000 | Muschler | |
| 6,200,606 B1 | 3/2001 | Peterson | |
| 6,333,029 B1 | 12/2001 | Vyakarnam | |
| 6,365,149 B2 | 4/2002 | Vyakarnam | |
| 6,534,084 B1 | 3/2003 | Vyakarnam | |
| 6,541,024 B1 | 4/2003 | Kadiyala | |
| 6,544,290 B1 | 4/2003 | Lee | |
| 6,811,776 B2 | 11/2004 | Kale | |
| 6,852,330 B2 | 2/2005 | Bowman | |
| 2003/0114936 A1* | 6/2003 | Sherwood et al. | 623/23.58 |
| 2003/0149437 A1 | 8/2003 | Livne | |
| 2005/0074877 A1* | 4/2005 | Mao | 435/366 |
| 2005/0177249 A1* | 8/2005 | Kladakis et al. | 623/23.74 |

FOREIGN PATENT DOCUMENTS

| | | | | |
|---|---|---|---|---|
| WO | WO2007/115123 A2 * | 10/2007 | | G06F 11/00 |
| WO | WO 2007115123 A2 * | 10/2007 | | G06F 11/00 |

OTHER PUBLICATIONS

Schwartz et al. Ability of Commercial Demineralized Freeze-Dried Bone Allograft to Induce New Bone Formation. J Periodontol 1996;67:918-926.*
Fennema et al. The effect of bone marrow aspiration strategy on the yield and quality of human mesenchymal stem cells. Acta Orthopaedica 2009; 80 (5): 618-621.*
Travlos. Normal Structure, Function, and Histology of the Bone Marrow. Toxicologic Pathology, 34:548-565, 2006.*
Srouji et al. Microscopy Analysis of Bone Marrow-Derived Osteoprogenitor Cells Cultured on Hydrogel 3-D Scaffold. Microscopy Research and Technique 66:132-138 (2005) (Year: 2005).*
Gerasimov et al., 1986 Differentiation potentials of clonal strains of bone marrow fibroblasts. Biull Eksp Bioi Med. I0I:717-9.
Gotoh Y, Hiraiwa K, Nagayama M.1990 In vitro mineralization of osteoblastic cells derived from human bone. Bone Miner. 8:239-50.
Hofmann GO,etal.,1998 Bridging long bone and joint defects with allogeneic vascularized transplants.Langenbecks Arch Chir Suppl Kongressbd.115:1285-7.
Johnson DR.2000 Differential expression of human major histocompatibility class I loci: HLA-A,-B,and-C. HumImmunol.61:389-96.
Kadiyala S,et al.1997 Culture expanded canine mesenchymal stem cells possess osteochondrogenic potential in vivo and in vitro. CellTransplant.6:125-34.
Koc et al.1999 Bone marrow-derived mesenchymal stem cells remain host-derived despite successful hematopoietic engraftment. Exp Hematol. 27:1675-81.
Nade S, et al. 1983 Osteogenesis after bone and bone marrow transplantation. Clin Orthop Relat Res. 181:255-63.
Neppert J, Nunez G, Stastny P. 1984 HLA-A, B, C; -DR; -MT, -MB, and SB antigens on unstimulated human endothelial cells. Tissue Antigens. 24:40-7.
Niemeyer P, et al. 2004 Allogenic transplantation of human mesenchymal stem cells for tissue engineering purposes: an in vitro study. Orthopade. 33:1346-53.
Petersen BE, et al. 1999 Bone marrow as a potential source of hepatic oval cells. Science. 284:1168-70.
Shang Q, et al. 2001 Tissue-engineered bone repair of sheep cranial defects with autologous bone marrow stromal cells. J Craniofac Surg. 12:586-93.
Sottile V, Thomson A, McWhir J. 2003 In vitro osteogenic differentiation of human ES cells. Cloning Stem Cells. 5:149-55.
Sun S, Guo Z, Xiao X, Liu B, Liu X, Tang P H, Mao N. 2003 Isolation of mouse marrow mesenchymal progenitors by a novel and reliable method. Stem Cells. 21:527-35.

(Continued)

*Primary Examiner* — Taeyoon Kim
(74) *Attorney, Agent, or Firm* — Browdy and Neimark, PLLC

(57) ABSTRACT

A prosthetic implant comprising a biocompatible three-dimensional scaffold and at least two cell types selected from the group consisting of osteoblasts, osteoclasts, and endothelial cells or progenitors thereof.

18 Claims, 21 Drawing Sheets

(56) References Cited

OTHER PUBLICATIONS

Theunissen et al 2005 A multifactorial analysis of umbilical cord blood, adult bone marrow and mobilized peripheral blood progenitors. Exp Hem. 33:165-72.
Winston D J, Ho WG, Champlin RE. 1990 Cytomegalovirus infections after allogeneic bone marrow transplantation. Rev Infect Dis. 12 Suppl 7:S776-92.
Aggarwal S, Pittenger MF. 2005 Human mesenchymal stem cells modulate allogeneic immune cell responses. Blood. 105:1815-22.
Bielby RC, Boccaccini AR, Polak JM, Buttery LD. 2004 In vitro differentiation and in vivo mineralization of osteogenic cells derived from human embryonic stem cells. Tissue Engineering. vol. 10, 9/10, p. 1518-1525.
Bruder SP, et al. 1998a The effect of implants loaded with autologous mesenchymal stem cells on the healing of canine segmental bone defects. J Bone Joint Surg Am.80:985-96.
Bruder SP, et al., 1998b Bone regeneration by implantation of purified, culture-expanded human mesenchymal stem cells. J Orthop Res. 16:155-62.
Buttery LD, et al. 2001 Differentiation of osteoblasts and in vitro bone formation from murine embryonic stem cells. Tissue Eng. 7:89-99.
Chakrabarti S, et al., 2002 Adenovirus infections following allogeneic stem cell transplantation. Blood, 100:1619-27.
Chakrabarti S, et al., 2004. Adenovirus Infections in Stem Cell Transplant Recipients. Leukemia & Lymphoma, vol. 45 (5), pp. 873-885.
Choi K, Kennedy M, Kazarov A, Papadimitriou JC, Keller G. 1998 A common precursor for hematopoietic and endothelial cells. Development. 125:725-32.
Cinotti G, et al., 2004 Experimental posterolateral spinal fusion with porous ceramics and mesenchymal stem cells. J Bone Joint Surg Br. 86: 135-42.
Cohen Y, Nagler A. 2004 Umbilical cord blood transplantation—how, when and for whom? Blood Rev. 18:167-79.
Gang EJ,etal.,2004 In vitro mesengenic potential of human umbilical cord blood-derived mesenchymal stem cells. Biochem Biophys Res Commun. 321:102-8.
Hamaguchi et al.,1999 In vitro hematopoietic and endothelial cell development from cells expressing TEK receptor in murine aorta-gonad-mesonephros region. Blood 93:1549-56.
He Z, Huang S, Li Y, Zhang Q. 2002 Human embryonic stem cell lines preliminarily established in China. Zhonghua Yi Xue Za Zhi. 82:1314-8.
Horwitz et al.,1999 Transplantability and therapeutic effects of bone marrow-derived mesenchymal cells in children with osteogenesis imperfecta. Nat Med. 5:309-13.
Horwitz et al. 2001Clinical responses to bone marrow transplantation in children with severe osteogenesisi mperfecta. Blood. 97:1227-31.
Horwitz et al.2002 Isolated allogeneic bone marrow-derived mesenchymal cells engraft and stimulate growth in children with osteogenesis imperfect. PNAS.99:8932-7.
Hovatta et al.2003 A culture system using human foreskin fibroblasts as feeder cells allows production of human embryonic stem cells. Hum Reprod.18:1404-9.
Jaiswal et al.,1997 Osteogenic differentiation of purified, culture-expanded human mesenchymal stem cells in vitro. 1. Cell Biochem. 64:295-312.
Kawaguchi H,et al. 2004 Enhancement of periodontal tissue regeneration by transplantation of bone marrow mesenchymal stem cells. 1 Periodontol. 75:1281-7.
Krampera et al.2003 Bone marrow mesenchymal stem cells inhibit the response of naive and memory antigen•specific T cells to their cognate peptide. Blood 101:3722-9.
Lane et al.1999 Bone marrow and recombinant human bone morphogenetic protein-2 in osseous repair.Clin Orthop. 61:216-27.

Lee OK, Kuo TK, Chen WM, Lee KD, Hsieh SL, Chen TH. 2004 Isolation of multipotent mesenchymal stem cells from umbilical cord blood. Blood. 103:1669-75.
Lee WY et al.2002 The effect of bone marrow transplantation on the osteoblastic differentiation of human bone marrow stromal cells. J Clin Endocrinol Metab. 87:329-35.
Lewandrowski et al. 2000 Bioresorbable bone graft substitutes of different osteoconductivities. Biomaterials. 21:757-64.
Maitra B et al. 2004 Human mesenchymal stem cells support unrelated donor hematopoietic stem cells and suppress T-cell activation. Bone Marrow Transplant. 33:597-604.
Mitchell KE,et al. 2003 Matrix cells from Wharton's jelly form neurons and glia. Stem Cells.21:50-60.
Mizuno H, Hyakusoku H. 2003 Mesengenic potential and future clinical perspective of human processed lipoaspirate cells. J Nippon Med Sch. 70:300-6.
Murohara T, et al. 2000 Transplanted cord blood-derived endothelial precursor cells augment postnatal neovascularization. J Clin Invest. 105:1527-36.
Ohgushi et al. 1990 Marrow cell induced osteogenesis in porous hydroxyapatite and tricalcium phosphate. J Biomed Mater Res. 24:1563-70.
Pereira et al. 1995 Cultured adherent cells from marrow can serve as long•lasting precursor cells for bone, cartilage, and lung in irradiated mice. PNAS, 92:4857-61.
Ringe J, et al.. 2002 Porcine mesenchymal stem cells. Induction of distinct mesenchymal cell lineages. Cell Tissue Res. 307:321-7.
Schmidt et al. 1991 A randomized, controlled trial of prophylactic ganciclovir for cytomegalovirus pulmonary infection; N Engl J Med. 1991324:1005-11.
Valimaki et al. 1999 A prospective study of bone loss and turnover after allogeneic bone marrow transplantation. Bone Marrow Transplant. 23:355-61.
Wakitani et al. 2003 Embryonic stem cells injected into the mouse knee joint form teratomas and subsequently destroy the joint. Rheumatology, 42:162-5.
Wang HS, et al. 2004 Mesenchymal stem cells in the Wharton's jelly of the human umbilical cord. Stem Cells. 22:1330-7.
Werntz JR, Lane JM, Burstein AH, Justin R, Klein R, Tomin E. 1996 Qualitative and quantitative analysis of orthotopic bone regeneration by marrow. J Orthop Res. 14:85-93.
Yoshikawa T, Ohgushi H. 1999 Autogenous cultured bone graft—bone reconstruction using tissue engineering approach. Ann Chir Gynaecol. 88:186-92.
Zuk PA, et al. 2001 Multilineage cells from human adipose tissue: implications for cell-based therapies. Tissue Eng. 7:211-28.
Zuk PA, et al. 2002 Human adipose tissue is a source of multipotent stem cells. Mol Biol Cell.13:4279-95.
zur Nieden NI, Kempka G, Ahr HJ. 2003 In vitro differentiation of embryonic stem cells into mineralized osteoblasts. Differentiation. 71:18-27.
http://chem.wisc.edu/deptfiles/genchem/sstutorial/FunChem.htm; Elizabeth Rogers, Iris Stovall, Loretta Jones, Ruth Chabay, Elizabeth Kean, Stanley Smith, Falcon Software, Inc, (c)Copyright 2000.
Dominici M. et al; "Minimal criteria for defining multipotent mesenchymal stromal cells. The International Society for Cellular Therapy position statement"; Cytotherapy, vol. 8, No. 4, pp. 315-317, 2006. (3 pages).
Crockett J.C. et al; "Bone remodelling at a glance"; Journal of Cell Science 124, pp. 991-998, 2011 (8 pages).
Bodine P.; "Wnt signaling control of bone cell apoptosis"; Cell Research 18, pp. 248-253, 2008. (6 pages).
Bohm A.M. et al; "Recruitment of osteogenic cells to bone formation sites during development and fracture repair"; Neues aus der Forschung, 2016. (5 pages).
Lian J.B. et al; "Runx2/Cbfa1: A Multifunctional Regulator of Bone Formation"; Current Pharmaceutical Design, 9, pp. 2677-2685, 2003 (10 pages).

* cited by examiner

BONE-LIKE PROSTHETIC IMPLANTS

CROSS-REFERENCE TO RELATED APPLICATIONS

This application is the U.S. national phase application of PCT International Application No. PCT/IL2009/000395, filed on Apr. 7, 2009, which claims the benefit of priority from U.S. Provisional Application Ser. No. 61/071,064, filed on Apr. 10, 2008, and from U.S. Provisional Application Ser. No. 61/136,557, filed on Sep. 15, 2008, all of which are hereby incorporated by reference in their entirety.

FIELD OF THE INVENTION

The present invention relates to the field of bone, cartilage and hard tissue prosthetics, and more particularly to the use of cellular-based implants for the preparation of prosthetic implants for bone replacement and repair, cartilage replacement and repair, and for other hard tissue applications.

BACKGROUND OF THE INVENTION

The repair of outsized deficiencies, typically defined as gaps of at least about 2.4 mm in size, in the diaphyseal, craniomaxillofacial and other skeletal bones is a considerable problem in orthopedic surgery.

In 1998, about 300,000 bone-graft procedures were performed in the United States alone. This number increased to approximately 450,000 by the year of 2000, when the number of bone grafting procedures performed worldwide exceeded 2.2 million (Lewandrowski et al, 2000). Of the 300,000 procedures performed in 1998, 90% involved the use of either autologous grafts (i.e. using tissue from another part of the body of the patient), or of allografts (i.e. using tissue from a live human donor or cadaver). Therefore, a phase of tissue harvest from the patient or from a donor is required.

The tissue harvesting is executed by a surgical procedure usually involved collecting tissue from the iliac crest, the distal femur, the proximal tibia, the fibula, or from other small bones. The harvested tissue is restructured and transplanted at the damaged site.

However, the graft-harvesting procedures are associated with considerable morbidity and substantial pain. Tissue harvesting for an autologous grafts or from live donors for an allograft may also result in complications such as inflammation, infection, or even death. Allografts taken from live donors or cadavers also carry risks of disease transmission and although grafts are subjected to protective and sterilization treatments such as tissue freezing, freeze-drying, gamma irradiation, electron beam radiation, and ethylene oxide, this risk is not completely removed. Furthermore, substantial supply problems exist, as the bone tissues harvested are limited.

The limited supply and inherited harvesting complications have inspired the development of alternative strategies for the repair of significant bone defects.

The use of 3-dimensional (3-D) bone substitutes such as bone extract, polymer or mineral scaffolds as implants has been investigated and porous biocompatible scaffolds have been used for the repair and regeneration of bone tissue.

Early attempts at tissue repair have focused mainly on the use of amorphous, biocompatible foam as porous plugs to fill large voids in bone. U.S. Pat. No. 4,186,448 described the use of porous mesh plugs composed of polyhydroxy acid polymers, such as polylactide, for healing bone voids. Several different methods for making other scaffolds were also described (i.e. U.S. Pat. Nos. 5,133,755; 5,514,378; 5,522,895; 5,607,474; 5,677,355; 5,686,091; 5,716,413; 5,755,792; 5,769,899; 5,770,193; 6,333,029; 6,365,149 and 6,534,084).

Bone marrow (BM) has been shown to contain population of cells that possess osteogenic potential. As such, an alternative to the scaffold-osteoinductive approach is to transplant into patients living cells that possess this capacity.

Cytokine-manipulated, naïve autologous and allogeneic BM cells have successfully healed diffracted or resorbed bones in experimental models (Werntz et al, 1996; Lane et al, 1999; Nilsson et al, 1999; Kawaguchi et al, 2004) and human patients (Horwitz et al, 1999; Horwitz et al 2001, 2004).

These techniques were further developed by using enriched mesenchymal cells for transplantation, and were demonstrated to be successful in animal models and human patients (Pereira et al, 1995; Shang et al, 2001; Horwitz et al, 2002). Accordingly, U.S. Pat. Nos. 5,716,616 and 6,200,606 describe experimental therapies for treating bone loss syndromes that are based on the implantation of fresh stromal cells isolated from autologous or syngeneic individuals to recipients (i.e. U.S. Pat. No. 5,716,616). Although this approach is promising in theory, it is difficult in practice to obtain the sufficient quantities of BM having the requisite number of osteoprogenitor cells.

Tissue Induction methods (TI) have been developed, wherein tissue regeneration occurs through in-growth of surrounding cells into 3-D scaffolds. The limitations of the TI procedure include the requirement for scaffolding material that possesses both TI capability and mechanical properties similar to those of autologous bone tissues.

Another approach to bone tissue generation is referred to as "complex cell transplantation", which combines scaffold technology with cell cultivation techniques. In its simplest form, autologous BM aspirate is passed through a biocompatible, implantable substrate placed intra-peritoneally to provide a composite bone graft (Nade et al, 1983 and U.S. Pat. Nos. 5,824,084; 6,049,026).

Alternatively, progenitor cells of the osteogenic lineage are seeded onto biocompatible (biodegradable or non-biodegradable) scaffolds in the presence or absence of growth promoting factors (U.S. Pat. Nos. 6,541,024; 6,544,290; 6,852,330). Transplantation into affected patients is performed following an ex-vivo expansion phase of the cells on the given scaffold. Using this approach, either primary osteogenic cells or expanded Mesenchymal Stromal Cells (MSC) layered upon ceramic scaffolds was able to regenerate bone tissue (Kadiyala et al, 1997; Bruder et al, 1998a, b; Cinotti et al, 2004).

However, experimental results revealed a number of disadvantages of those complex cell transplantations. Firstly, bone marrow transplantation (BMT) in human patients is associated with a general decrease in the skeletal mineral density (Valimaki et al, 1999). Secondly, it was demonstrated that after BMT, although peripheral mononuclear cells (MNC) in the recipients are of donor origin, the BM stroma cells and MSCs are basically of the recipient origin (Koc et al, 1999; Lee et al, 2002). Finally, during the first year follow-up of bone marrow transplanted patients, a gradual decrease in bone repair was evident and significant loss of donor MSC was observed (Lee et al, 2002).

Living bone is a continuously evolving organ and in the normal course of bone maintenance, a remodeling process is being employed. In those procedures, Old bone is being replaced by new bone and the organ responds to its environment changing requirements for strength and elasticity. Therefore, normal remodeling progression requires that the mechanical loading processes of bone resorption and bone formation procedures are tightly coordinated.

In cellular terms, this depends on sequential functioning of osteoclasts (bone resorbing cells) and osteoblasts (bone forming cells). In addition, endothelial cell and endothelial cell precursors (angioblasts) are required to form the new blood vessels in the developed bone tissue. Yet, the various cell types participating in bone formation are of different lineages. It is now known that osteoblasts stalk from mesenchymal stem cells, while osteoclasts (directly originating from Hematopoietic Stem Cells (HSC)) and endothelial cells are descendents of a common blast colony-forming cell (Choi et al, 1998; Hamaguchi et al, 1999). As such, methodologies for ex-vivo production of bone-like material that rely on osteoblasts as the exclusive cellular component suffer from an inherited fault.

It would be highly advantageous to have a material for use in repairing bone lesions that is devoid of at least some of the limitations of the prior art.

External fixation devices for keeping fractured bones stabilized and aligned, and ensuring that the bones remain at an optimal position during the healing process are known and commonly used. Such devices typically comprise a plurality of pins placed proximal and distal to the fracture, fixed in a surrounding external mechanical assembly.

External fixation devices are also used for reconstructive orthopedics, such as treatment of bone losses and defects. In such cases the device can either remain in place until healing occurs and then to be removed, leaving no foreign material inside the bone, or it can totally or partially remain inside the bone.

External fixation devices are further useful in experimental models of bone repair which have been developed for a variety of purposes, including the investigation of factors influencing fracture repair, and development of improved methods of managing fractures in human and animals. Such models make use of long bones of large experimental animals, whose weight is more than 40 gr, such as dogs, sheep, rabbits and rats. The term long bone refers to bones in which the length is greater than the width, such as a femur, a tibia, a humerus and a radius.

US application No. 20030149437 to the same inventors as the present application discloses a method of repairing a long bone having a defect. The method comprising mechanically fixating the long bone or portions thereof and filling the defect with a biodegradable scaffold impregnated with growth factors and/or cells to cause a regeneration of the bone.

SUMMARY OF THE INVENTION

The present invention provides an ideal solution for the ex-vivo regeneration of remodeled bone, cartilage and other hard tissue applications. The background art describes bone substitutes made from cells of osteogenic lineage cultured on 3-D scaffold. In contrast with this art, the present invention manipulates co-culture and multi-cell cultures made up of two or more independent cell types growing on 3-D scaffolds to optimize the bone regeneration and remodeling processes, preferably through a flow system and more preferably to grow cells at a high density.

Unless otherwise defined, all technical and scientific terms used herein have the same meaning as commonly understood by one of ordinary skill in the art to which this invention pertains. In case of conflict, the patent specification, including definitions, will control.

As used herein the phrase "three dimensional cultures" refers to cultures in which the cells are disposed to conditions which are compatible with cell growth while allowing the cells to grow in more than one layer. It is well appreciated that the in situ environment of the cells in living organism (or a tissue) is in a three dimensional architecture. Cells are surrounded by other cells. They are held in a complex network of extra cellular matrix nanoscale fibers that allows the establishment of various local microenvironments. Their extra cellular ligands mediate not only the attachment to the basal membrane but also access to a variety of vascular and lymphatic vessels. Oxygen, hormones and nutrients are ferried to cells and waste products are carried away. The conditions in the three dimensional culture of the invention are designed to mimic such an environment as is further exemplified below. Thus, the three-dimensional scaffold of the present invention is differed and preferred to any type of two-dimensional artificial cell environments.

It will be appreciated that the conditions of the three-dimensional culture are such that enable the expansion of the adherent cells.

As used herein the terms "expanding" and "expansion" refer to substantially differentiation-less maintenance of the cells and ultimately cell growth, i.e., increase of a cell population (e.g., at least 2 fold) without differentiation accompanying such increase.

As used herein the terms "maintaining" and "maintenance" refer to substantially differentiation-less cell renewal, i.e., substantially stationary cell population without differentiation accompanying such a stationary state.

As used herein, the term "treating" includes abrogating, substantially inhibiting, slowing or reversing the progression of a condition, substantially ameliorating clinical or aesthetical symptoms of a condition or substantially preventing the appearance of clinical or aesthetical symptoms of a condition.

As used herein, the terms "comprising", "including", "having" and grammatical variants thereof are to be taken as specifying the stated features, integers, steps or components but do not preclude the addition of one or more additional features, integers, steps, components or groups thereof. These terms encompass the terms "consisting of" and "consisting essentially of".

The phrase "consisting essentially of" or grammatical variants thereof when used herein are to be taken as specifying the stated features, integers, steps or components but do not preclude the addition of one or more additional features, integers, steps, components or groups thereof but only if the additional features, integers, steps, components or groups thereof do not materially alter the basic and novel characteristics of the claimed composition, device or method.

As used herein, the indefinite articles "a" and "an" mean "at least one" or "one or more" unless the context clearly dictates otherwise.

According to some embodiments, there is provided a prosthetic implant comprising a biocompatible three-dimensional scaffold and at least two cell types selected from the group consisting of osteoblasts, osteoclasts, chondrocytes and endothelial cells or progenitors thereof. Optionally, the osteoblasts are derived from mesenchymal stem cells. Also optionally, the at least two cell types are obtained from a source selected from the group consisting of an autologous source, a syngeneic source and an allogeneic source. Preferably, the source comprises one or more of bone marrow, placenta, adipose tissue, cord blood, peripheral blood, mobilized peripheral blood, embryonic stem cells and the like.

Optionally the implant further comprises at least three different cell types selected from the group consisting of osteoblasts, osteoclasts, and endothelial cells or progenitors thereof. The progenitors are preferably selected from the group consisting of mesenchymal stromal cells, hematopoietic stem cells, and angioblasts.

Also optionally, the at least two cell types are selected from the group consisting of hematopoietic cells, vascular endothelial cells and mesenchymal cells and their progenitors.

Preferably, the 3-dimensional scaffold comprises a pre-shaped and sponge-like or porous and can e.g. comprise an organic, ceramic or metallic material, or comprises dry, frozen or dematerialized bone particles or comprises a polymer selected from the group consisting of aliphatic polyesters, poly(amino acids), co-poly(ether-esters), poly-alkylenes oxalates, polyamides, tyrosine derived polycarbonates, poly(iminocarbonates), polyorthoesters, polyoxaesters, polyamidoesters, polyoxaesters containing amine groups, poly(anhydrides), polyphosphazenes, bioactive glass, calcium phosphate derivatives, calcium sulfate derivatives, calcium hydroxyapatite, silicate matrices, hydroxyapatite, hyalauronic acid, beta-3 calcium phosphate, cross-linked collage fibers, resin based materials and combinations thereof.

More preferably, the 3-dimensional scaffold comprises a solid or gel like biodegradable polymer.

Optionally and most preferably, the biodegradable polymer is a natural polymer selected from the group consisting of alginate, chitosan, hyaluronan derivatives and collagen, and combinations thereof.

Also optionally and most preferably, the biodegradable polymer is selected from the group consisting of poly caprolactone, poly-glycolic acid, poly-lactic acid, poly lactic co-glycolic, poly tartonic acid, or co-polymers thereof and combinations thereof.

Optionally, the 3-dimensional scaffold comprises a biodegradable material. Alternatively and optionally, the 3-dimensional scaffold comprises a non-biodegradable material.

Optionally, the 3-dimensional scaffold has a pore size in the range of from about 50 microns to about 1000 microns.

Also optionally, the 3-dimensional scaffold features a coating layer comprising a material selected from the group consisting of poly-D-lysine, poly-L-lysine, collagen, fibronectin, Extracellular Matrix (ECM) and hydrogel, or a combination thereof.

The above implant may optionally be used to repair at least a portion of a bone lesion, which case the implant is optionally pre-shaped for insertion into the bone lesion.

According to other embodiments of the present invention, there is provided a method of producing a prosthetic implant, comprising isolating, expanding and co-cultivating of at least two cell types selected from the group consisting of mesanchymal stromal cells, osteoblasts, osteoclasts, chondrocytes and endothelial cells or progenitors thereof on a 3-dimensional scaffold.

Optionally the cells are arranged in a three-dimensional manner on the scaffold for improved growth and/or viability. The cells are preferably grown to high density. The cells are optionally grown to a density of at least $10^6$ cells/ml, preferably grown to a density of at least $5 \times 10^6$ cells/ml and more preferably grown to a density of at least $10^7$ cells/ml.

Also optionally the three-dimensional scaffold provides an environment supporting the growth of high density cell growth through the use of improved media flow.

Preferably the expansion is performed in a flow system allowing the growth of high density cultures, such as a bioreactor.

More preferably, the bioreactor comprises a growth matrix. Optionally, the growth matrix is in sheet form. Preferably, the sheet comprises non-woven fiber. Alternatively, the sheet comprises open-pore foamed polymers. More preferably, a thickness of the sheet is from about 50 to about 1000 microns. Most preferably, the sheet comprises pores having a diameter of from about 10 microns to about 100 microns. Optionally and most preferably, the sheet comprises fibers having a diameter of from about 0.5 microns to about 200 microns. Optionally, the diameter is from about 10 microns to about 20 microns.

Optionally the 3-dimensional scaffold is pre-shaped for implant into a bone lesion.

Optionally the mesenchymal cell isolation process comprises preparing samples of bone marrow, fat tissue, mobilized peripheral blood, placenta or cord vein obtaining a cell suspension, centrifuging the suspension; and collecting precipitated mesenchymal stromal cells and mesenchymal cells.

Optionally the hematopoietic and endothelial cell isolation process comprises preparing samples of bone marrow; fat tissue; peripheral blood; mobilized peripheral blood, cord blood, cord vein or placenta, obtaining a cell suspension, centrifuging the suspension; and collecting precipitated cells.

Optionally the co-cultivation step comprises subjecting the cells to an osteogenic stimulus.

Optionally the osteogenic stimulus comprises contacting the cells with a molecule selected from the group consisting of dexamethasone, sodium β-glycerophosphate, 1,25 dihydroxycholecalciferol calcitriol, and L-ascorbic acid-2-phosphate (10-500 nM). Preferably, the osteogenic stimulus comprises exposure to shear forces.

Optionally a concentration of the dexamethasone is in the range of from about 10 to about 200 nM.

Optionally a concentration of the sodium β-glycerophosphate is in the range of from about 5 to about 25 mM.

Optionally, a concentration of the 1,25 dihydroxycholecalciferol calcitriol is in the range of from about 5 to about 50 nM.

Optionally the co-cultivation step is carried out in a medium comprising at least one of a growth factor and a cytokine.

Preferably the growth factor or cytokine is selected from the group consisting of transforming growth factor beta (TGF beta), insulin-like growth factor-1 and 2 (IGF-1 and 2), PDGF (platelet derived growth factor), osteogenic protein-1 (OP-1), fibroblast growth factor (FGF), FGF-2, FGF-9, FGF-10, PTH (parathyroid hormone), PRP (platelet rich plasma), EGF (epidermal growth factor), VEGF (vascular endothelial growth factor) and a Bone Morphogenic Protein (BMP) family member. More preferably, the bone morphogenic protein is selected from the group consisting of BMP-2, BMP-4 and BMP-7.

According to other embodiments, there is provided an implant constructed according to any method described herein.

BRIEF DESCRIPTION OF THE FIGURES

Some embodiments of the invention are herein described, by way of example only, with reference to the accompanying figures. The description, together with the figures, makes apparent how embodiments of the invention may be practiced to those skilled in the art. It is stressed that the particulars shown in the figures are by way of example and for purposes of illustrative discussion of embodiments of the invention.

In the figures:

FIGS. 18B-21 schematically illustrate a process of a creation of the CSD in a femur of a small animal.

DESCRIPTION OF EMBODIMENTS

Figure 1:
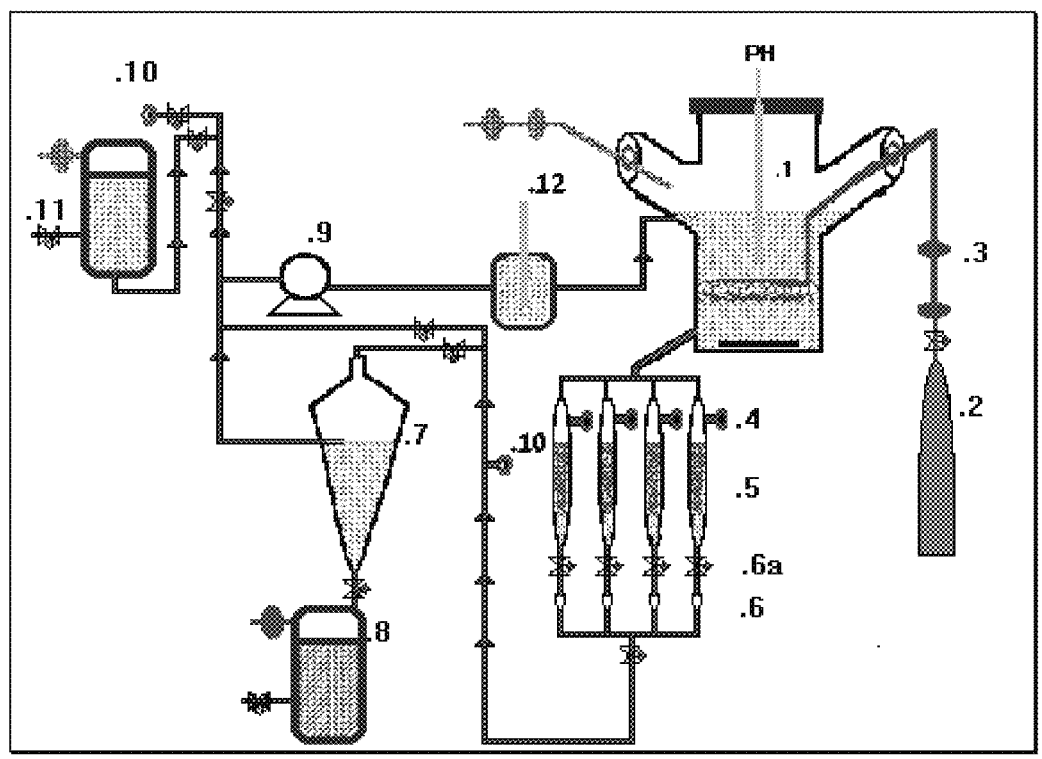
FIG. 1 illustrates a bioreactor system for growth of cells in accordance with the principles of the present invention.

The present invention, in at least some embodiments, provides a prosthetic implant comprising a biocompatible 3-dimensional scaffold and at least two cell types selected from the group consisting of osteoblasts, osteoclasts, chondrocytes, and endothelial cells, or progenitors thereof.

The use of at least two cell types is in sharp contrast with prior art that depends upon expansion of only one type of progenitor cells—namely, the pre-osteoblasts, such as disclosed in U.S. Pat. No. 6,811,776.

The present invention also provides, in at least some embodiments, a method of producing the prosthetic implant described above, the method comprising the steps of isolation, expansion and co-cultivation of at least two types of cells onto a 3-dimensional scaffold.

The 3-D scaffolds are pre-fabricated to the required size and shape. A plurality of cells and stem cell from different sources (MSC or mesenchymal stem cells together with HSC or hematopoietic stem cells and/or endothelial cells) in pre-determined ratios are preferably first cultivated and expanded separately. Next they are preferably cultivated and co-expanded ex vivo under sterile conditions on the 3-D scaffold, using conventional culture medium, such as DMEM, RPMI, with supplements of human serum (from autologous or allogeneic sources) or animal serum, or in serum-free media that allows the attachment and growth of adherent cells. Culture medium that supported the initial growth and expansion phase of these cells may optionally be replaced by another cell culture formula that supports the differentiation of these cells and bone formation.

HSC are seeded onto the founding 3-D culture system, which is the 3D scaffold containing the MSC and osteoblasts with or without endothelial cells and/or endothelial progenitors, in a fixed ratio. Alternatively, HSC are seeded simultaneously or substantially simultaneously with the MSC and osteoblasts, with or without endothelial cells. A preferred ratio of non-HSC to HSC is between 5:1 to 5000:1, respectively. More preferentially, the ratio is between 20:1 to 300:1. According to experimental evidence performed by one or more of the inventors, these ratios were shown to be preferred (data not shown). For the mere expansion of the cells and stem cells, serum-free or serum-containing media are employed. During the expansion phase, serum-containing media is preferably free of supplemented bioactive molecules of the following groups—hormones, growth factors, chemokines and cytokines.

To promote downstream differentiation of the expanded cells into bone forming cells needed in order to create the bone-like prosthetics, co-cultures grown as previously described may be exposed to osteogenic stimuli. These may include the mere presents of shear forces generated in the flow-through bioreactor system and/or a culture differentiation medium that contains, for example, one or more of the following molecules: dexamethasone, calcitriol (vitamin D derivative), sodium β-glycerophosphate and L-ascorbic acid-2-phosphate.

Optionally, the growth medium may be supplemented with growth factors and cytokines, such as, for example, one or more of: transforming growth factor beta (TGF beta), insulin-like growth factor-1 (IGF-1), osteogenic protein-1 (0P-1), fibroblast growth factor (FGF) members like FGF-2, FGF-9 and FGF-10 and members of bone morphogenic proteins (BMP) especially BMP-2, BMP-4 and BMP-7.

Preferably, the entire implant is then transplanted into a pre-determined site of bone loss.

Exemplary, illustrative non-limiting applications of such implants and/or prostheses and/or procedures according to the present invention include bone replacement, bone augmentation (for example in cases of bone weakness, osteoporosis and/or other conditions in which bone matter is reduced but not necessarily missing), dental applications (which may optionally relate to replacement for bone loss and/or bone augmentation), specific bodily areas of replacement such sinuses in which semi solid media or gel may optionally be used as scaffold rather than a rigid scaffold (which may then optionally spread to fill the area), combined bone/cartilage applications (in which the scaffold may optionally combine both types of structures, which may optionally be separated within the scaffold, for example for treatment of joints including but not limited to knees, elbows, ankles etc), plastic surgery applications, bone or cartilage repair, cartilage replacement, orthopedic applications and other hard tissue applications, or cartilage applications alone. Cartilage is optionally prepared from allogeneic materials.

The implants may optionally be prepared freshly for each application and/or may optionally be kept frozen in liquid nitrogen for example before use. Also the implants may optionally be partially prepared and then finished at the time of use, for example to permit the use of autologous cells from the subject to be treated.

Cells are preferably expanded and co-cultivated in a dedicated bioreactor system. The preliminary results presented in the Examples section below demonstrating that a dynamic flow system, such as a bioreactor for example, stimulates optimal cell density and cell viability in a 3-D construct, which is preferred for successful in-vivo implantation.

FIG. 1 illustrates a sample for plug flow bioreactor system may be use for the growth of cells in accordance with the principles of the present invention.

The bioreactor is described in detail in U.S. Pat. No. 6,911,201, which is incorporated by reference as if fully set forth herein. In this patent, a plug flow bioreactor system which allows the growth and prolonged maintenance of high density stromal cells cultures, that closely mimics the 3D bone marrow microenvironment. The cells were seeded on porrosive (ie having pores) inorganic carriers made of a non woven fabric matrix of polyester, enabling the propagation of large cell numbers in a relatively small volume. The structure and packing of the carrier have a major impact on oxygen and nutrient transfer, as well as on local concentrations and released stromal cell products (e.g., ECM proteins, cytokines). In addition, the capacity of the mesenchymal and stromal cells cultured in this system to promote the maintenance and expansion of transplantable human hemopoietic stem cells has been determined to be far superior over prior art methods.

The bioreactor comprises a medium reservoir 1; gas mixture container 2; gas filters 3; injection points 4; 5 plugs or containers of various sized plugs containing a pre-shaped 3-D scaffold; flow monitors 6; flow valves 6a; conditioned medium collecting and separating container 7; container for medium exchange 8; peristaltic pump 9; sampling point 10; container for medium exchange 11; monitor 12; steering device 14; and pH probe.

Preferably a continuous flow system is used. However, it should be understood that any controlled flow system could be used in place of the bioreactor of FIG. 1, which is intended as a non-limiting, illustrative example only. Flow, adequate but not excessive, levels of dissolved oxygen, control of pH, glucose level and temperature are the most important components of such a system. For example, the bioreactor may optionally be implemented according to the PluriX™ Bioreactor (Pluristem, Haifa, Israel), New Brunswick bioreactors and controlled stir tanks or rolling bottles system.

The flow system or bioreactor described herein includes the preferred features of supporting 3-D MSCs cultures with a continuous flow system. The plug-flow bioreactor described herein is capable of supporting the long-term growth of primary human MSC, osteoblasts, endothelial and HSC 3-D multi cells-cultures.

The use of 3-D multi cells-cultures in the bioreactor is not only essential for the establishment of superior cell-cell contact (via unique "niches" and cell-cell, cell-ECM interactions), but also for the production of known and novel soluble and membrane-bound cytokines. The 3-D multi cell culture can facilitate the supplementation of such bioreactors with appropriate cytokines, by using genetically engineered cytokine-producing variants.

In sharp distinction to background art methods, the bioreactor of the present invention employs a growth matrix that substantially increases the available attachment surface for the adherence of the MSCs, osteoblasts, endothelial and HSCs so as to mimic the mechanical infrastructure of bone microenvironment and allows in vitro bone formation. The growth matrix comprises a porous material as described in greater detail below. For example, for a growth matrix of 0.5 mm in height, the increase is by a factor of at least from 5 to 30 times, calculated by projection onto a base of the growth matrix. Such an increase by a factor of about 5 to 30 times, is per unit layer, and if a plurality of such layers, either stacked or separated by spacers or the like, is used, the factor of 5 to 30 times applies per each such structure.

When the matrix is used in sheet form, preferably nonwoven fiber sheets, or sheets of open-pore foamed polymers, the preferred thickness of the sheet is about 50 to 1000 μm or more, there being provided adequate porosity for cell entrance, entrance of nutrients and for removal of waste products from the growing tissues.

According to a preferred embodiment the pores have an effective diameter of 10 μm to 100 m. Such sheets can be prepared from fibers of various thicknesses, the preferred fiber thickness or fiber diameter range being from about 0.5 μm to 20 μm, still more preferred fibers are in the range of 10 μm to 15 μm in diameter.

The matrix sheets may also be cut, punched, or shredded to provide particles with projected area of the order of about 0.2 mm² to about 10 mm², with the same order of thickness (about 50 to 1000 μm).

The structures of the 3D scaffolds according to some embodiments of the present invention may be supported by, or bonded to, a porous support sheet or screen providing for dimensional stability and physical strength.

Thus a 3-D scaffold in concert with a dynamic flow bioreactor as illustrated in FIG. 1 provides for long-term cell viability of in vitro cultured cells seeded in 3D scaffolds which are intended for in vivo application.

Figure 2:
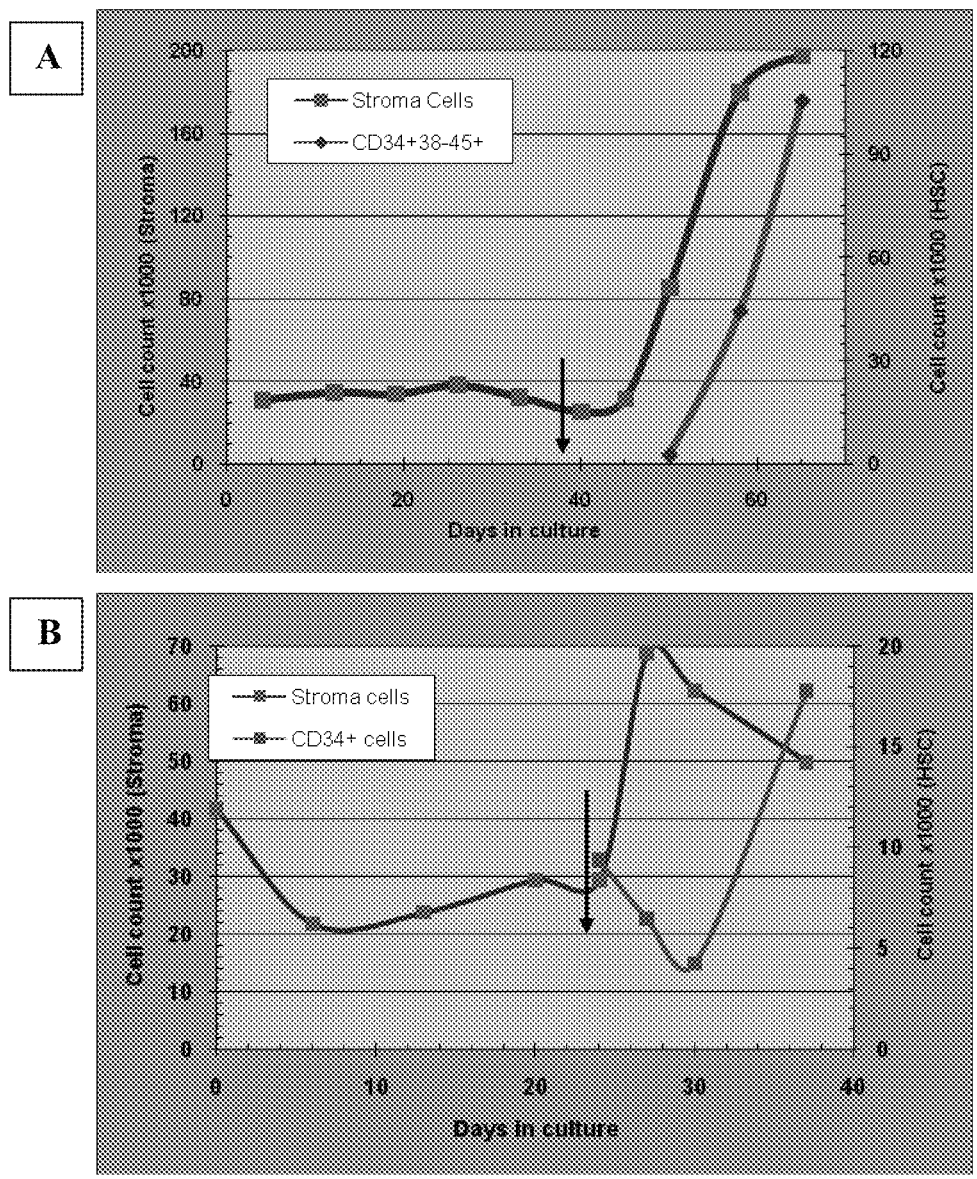
FIG. 2 shows the results of seeding BM-derived MSCs on the carrier in co-culture with hematopoietic progenitors cultured in 3-D dynamic flow system; demonstrate the cells 3-D co-culture interaction.
Figure 3:
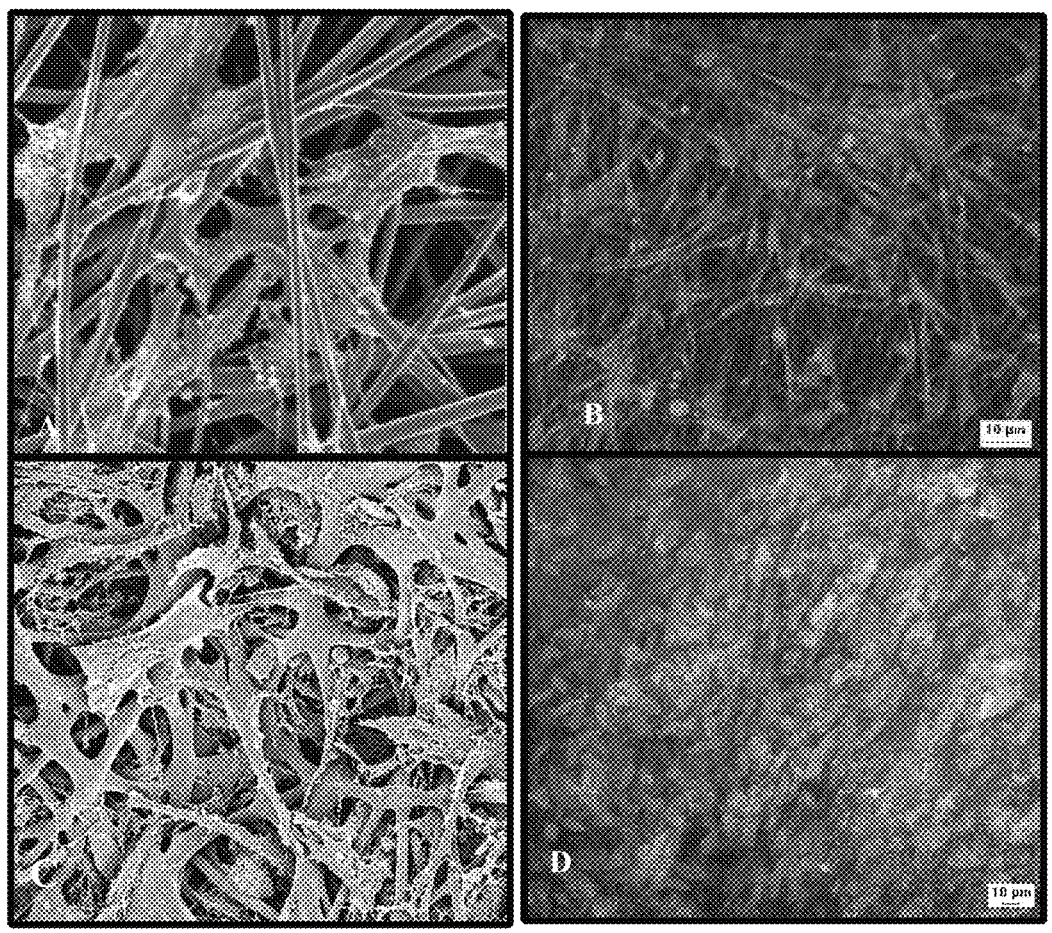
FIGS. 3 and 4 show Scanning Electron Microscope (SEM) and confocal micrographs of 3-D synthetic scaffold seeded with MSCs, cultured in dynamic flow system; demonstrate the cells density along and between the fibers.
Figure 4:
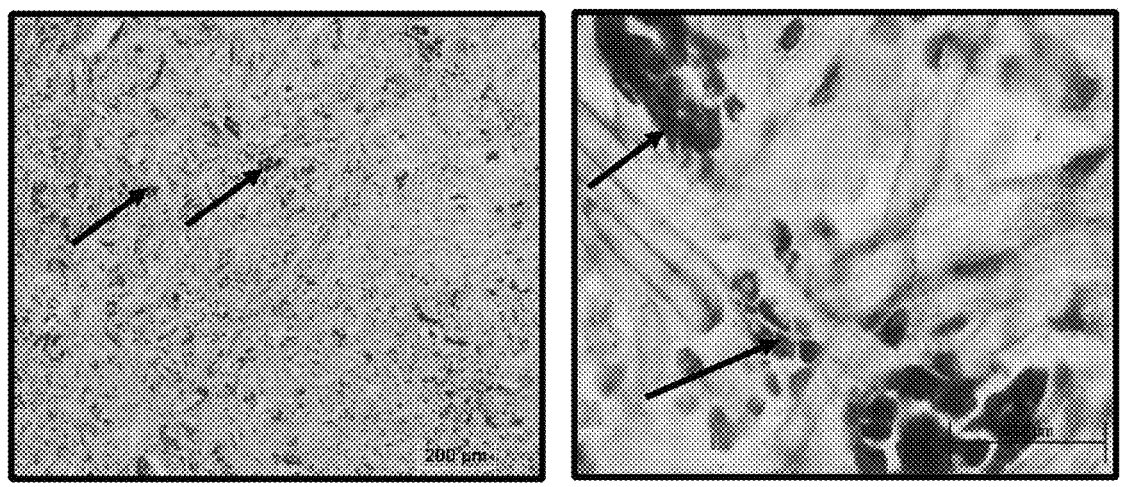

As shown in FIGS. 2-4, this growth system provides the necessary critical mass cell/volume and physiological milieu, including a constant supply of essential oxygen and nutrients, thus closely mimicking the in vivo conditions.

FIGS. 3 and 4 show Scanning electron microscope (SEM) and confocal micrographs of 3-D synthetic scaffold seeded with human MSCs cultured in dynamic flow system; demonstrate the cells density along and between the fibers.

The mesenchymal cells, osteoblasts, chondrocytes, endothelial and HSC that are used in various embodiments of the present invention are of autologous, syngeneic or allogeneic sources. For transplantation of hematopoietic or endothelial cells from allogeneic donor sources, HLA typing is performed and only sufficiently matched cells are being used. The most common cause of bone graft failure is graft rejection (Hoffmann et al, 1998). However, Mesenchymal cells and MSCs, express low levels of MHC antigens (Sun et al, 2003; Niemeyer et al, 2004) and MSC were shown to inhibit T-cell responses (Krampera et al, 2003; Maitra et al, 2004). Transplanted allogeneic Mesenchymal cells and MSCs could be detected in recipients at extended time points, indicating lack of immune recognition and clearance (Aggarwal and Pittenger, 2005). Accordingly, MSCs and Mesenchymal cells like osteoblasts and chondrocytes may be generated from autologous or allogeneic sources. Endothelial cells though expressing only low levels of HLA antigens (Neppert et al, 1984; Shahgasempour, 1998; Johnson, 2000) are immunogenic and could mediate vascular rejection (endothelialitis). This also applies for cells of the HSCs origin like osteoclasts. As such, according to the present invention and prior to the buildup of bone prosthetics from allogeneic sources, HLA repertoire on donor cells should be typed. Only closed matching allogeneic endothelial cells, HSCs and osteoclasts should be manipulated.

The 3-dimensional scaffold of the present invention comprises a non-toxic and biocompatible, biodegradable or non-biodegradable material, which may be prepared in three dimensions structure in order to support the growth of 3-dimensional cell cultures and promote guided tissue generation.

The scaffold preferably comprises a biocompatible polymer having pore size in the range of from about 50 to about 2000 microns, more in the range of from about 250 to about 750 microns. The physical environments that support the growth of the co-cultures on the said 3-D matrixes may be chosen from static systems involving cell culture grade flasks and dishes. However, culture of cells in scaffolds sufficiently large to bridge critical-sized defects is problematic. Simple diffusion may be unable to provide sufficient nutrients deep into large scaffolds. Consequently, under static culture conditions cells may preferentially proliferate at the scaffold periphery only. Under the growth conditions of the present invention, various alternative machineries could optionally and preferably be used to allow media flow and convey the culture media uniformly. These include but are not limited to stirred tanks, spinner flasks, rotary vessels, rolling bottles, rolling baskets and a perfusion plug flow or flow-through (plug flow) system (see example 1, FIG. 1 for details).

The 3-D scaffold of the present invention material can be powdered, semi solid or gel-like, so that it is suitable for use in implants that have no mechanical strength function requirements. However, the scaffold can also be substantially preshaped and sponge-like or porous and can e.g. comprise an organic, ceramic or metallic material and, as a function of the specific chosen carrier material, can fulfill a mechanical strength function and allow high density cells growth. The preshaped implant may also optionally be prepared by cutting or otherwise altering the structure of the 3-D scaffold to be suitable for the characteristics and requirements of the desired implant.

The 3-D scaffold of the present invention may optionally comprise dry, frozen or dematerialized bone particles or polymer selected from the group consisting of aliphatic polyesters, poly (amino acids), co-poly (ether-esters), poly-alkylenes oxalates, polyamides, tyrosine derived polycarbonates, poly (iminocarbonates), polyorthoesters, polyoxaesters, polyamidoesters, polyoxaesters containing amine groups, poly (anhydrides), polyphosphazenes, bioactive glass and calcium phosphate derivatives. Biodegradable polymers may also be used comprising natural biopolymers like alginate, chitosan, fibrin, fibronectin, hyaluronan derivatives and collagen. Biodegradable synthetic polymers may include derivatives such as poly caprolactone, polyglycolic acid, poly-lactic acid and poly lactic co-glycolic and poly tartonic acid.

The scaffold is preferably porous, having pore size of between 50 microns and 2000 microns. This range was found to be suitable according to experiments performed by one or more of the inventors, such that pores which are smaller than 50 microns do not permit the cells enter; pores larger than 2000 microns do not provide sufficient support for the 3D scaffold.

The implants need to have mechanical strength and require a more rigid structure which would presumably not be injectable. The implant may optionally be pre-shaped to the precise tissue gap size and structure and may be ready for transplantation into the lesion to be repaired. Optionally, the implant may be injectable and serve as a filler. As filler, the 3-B cultures may optionally and preferably be in an injectable form, such as a gel, semisolid or powder for example.

Exemplary embodiments of the invention are discussed herein below with reference to specific materials, methods and examples. The material, methods and examples discussed herein are illustrative and not intended to be limiting. In some embodiments, methods and materials similar or equivalent to those described herein are used in the practice or testing of embodiments of the invention. It is to be understood that the invention is not necessarily limited in its application to the details of construction and the arrangement of the components and/or methods set forth in the following description and/or illustrated in the drawings. The invention is capable of other embodiments or of being practiced or carried out in various ways.

EXAMPLES

Materials and Methods

Bioreactor: The bioreactor used in accordance with the teachings of the present invention was constructed in accordance with the design shown in FIG. 1, and described in detail above.

The glassware was designed and manufactured by the inventors and connected by silicone tubing (Degania, Israel).

The carriers for the cells were rotated overnight in phosphate buffered saline (PBS; Beit Ha'Emek Industries, Israel) without $Ca^{2+}$ and $Mg^{2+}$, followed by removal of the PBS and released debris.

Each column was loaded with 10 ml packed carrier. The bioreactor was filled with PBS without $Ca^{2+}$ and $Mg^{2+}$, all outlets were sealed and the system was autoclaved (120° C., 30 minutes). The PBS was removed via container [8] and the bioreactor was circulated in a 37° C. incubator with 300 ml Dulbecco's high-glucose medium (DMEM; GIBCO BRL) containing 10% heat-inactivated fetal calf serum (FCS; Beit Ha'Emek Industries, Israel) and a Pen-Strep-Nystatin mixture (100 U/ml:100 μg/ml:1.25 μn/ml; Beit Ha'Emek), for a period of 48 hours. Circulating medium was replaced with fresh DMEM containing the above +2 mM L-glutamine (Beit Ha'Emek).

MSCs/Stromal cells: Primary human marrow MSC and stromal cultures were established from aspirated stromal marrow of hematological healthy donors undergoing open-heart surgery. Alternatively MSC and stromal cultures were established from placenta or adipose tissues.

Bone marrow derived stromal cells—, marrow aspirates were 3-fold diluted in Hank's Balanced Salts Solution (HBSS; GIBCO BRL) and were subjected to Ficoll-Hypaque (Robbins Scientific Corp. Sunnyvale, Calif.) density gradient centrifugation. Marrow mononuclear cells (<1.077 gm/cm$^3$) were collected, washed 3 times in HBSS and resuspended in long-term culture (LTC) medium, consisting of DMEM (Beit Ha'Emek) supplemented with 12.5% FCS, 12.5% horse serum (Beit Ha'Emek), 10$^{-4}$ M β-mercaptoethanol (Merck) and 10$^{-6}$ mol/L hydrocortasone sodium succinate (Sigma). Cells were incubated in 25 ml tissue culture flasks (Corning) for 3 days at 37° C. (5% CO2) and then for 3 days at 33° C. (5% CO2) with weekly culture refeeding. Stromal cells from individual donors were employed for each bioreactor. Primary stromal cell cultures were split by trypsinization (0.25% Trypsin and EDTA in Puck's Saline A; Beit Ha'Emek) every 10 days, to allow sufficient cell expansion. Cultures were maintained at 33° C.-37° C. in LTC medium.

Placenta derived stromal cells—Inner parts of a full-term delivery placenta (Bnei Zion medical center, Haifa, Israel) were cut under sterile conditions, washed 3 times with Hank's Buffer and incubated for 3 h at 37° C. with 0.1% Collagenase (1 mg/ml tissue; Sigma-Aldrich, St. Lewis, Mo.). Using gentle pipeting, suspended cells were then washed with DMEM supplemented with 10% FCS, Pen-Strep-Nystatin mixture (100 U/ml:100 ug/ml:1.25 un/ml) and 2 mM L-glutamine, seeded in 75 cm$^2$ flasks and incubated at 37° C. in a tissue culture incubator under humidified condition with 5% CO$_2$. Thereafter, cells were allowed to adhere to a plastic surface for 72 hours after which the media was changed every 3-4 days. When reaching 60-80% confluence (usually 10-12 days), cells were detached from the growth flask using 0.25% trypsin-EDTA and seeded into new flasks. Cultured cells were thereafter collected for analysis or for culturing in bioreactors.

Adipose derived stromal cells—Stromal cells were obtained from human adipose tissue of liposuction procedures (Rambam Haifa, Israel). Adipose tissue was washed extensively with equal volumes of PBS and digested at 37° C. for 30 min with collagenase (20 mg/ml). Cells were then washed with DMEM containing 10% FCS, Pen-Strep-Nystatin mixture (100 U/ml:100 ug/ml:1.25 un/ml) and L-Glutamin and centrifuged at 1200 rpm for 10 min RT, resuspended with lysing solution (1:10; Biological Industries, Beit Ha'emek, Israel, in order to discard red-blood cells) centrifuged and resuspended with DMEM containing 10% FCS, Pen-Strep-Nystatin mixture (100 U/ml:100 ug/ml:1.25 un/ml) and L-Glutamin. Washed cells were then seeded in a sterile tissue culture medium flask at 3-10*10$^7$ cells/flask. At the next day cells were washed with PBS to remove residual RBC and dead cells. The cells were kept at 37° C. in a tissue culture incubator under humidified condition with 5% CO$_2$. The medium was changed every 3 to 4 days. At 60-80% confluence, the cells were detached from the growth flask using 0.25% trypsin-EDTA (Beit Ha'Emek) and seeded into new flasks.

Seeding of MSCs onto the 3-D cultures: 3-5 week MSCs were trypsinized and the cells washed 3 times in HBSS, resuspended in the bioreactor medium (see above), counted and seeded at 10$^6$ cells/ml in 10 ml volumes via an injection point ([4], FIG. 1) onto 10-100 ml 3-D carriers in the glass column of the bioreactor. Immediately following seeding, circulation was stopped for 0.25-24 hours to allow the cells to settle on the carriers. The cell growth in the bioreactor was monitored by analyzing the glucose demand of the cultures and by removal of carriers and cell enumeration by the MTT method (56). When the cells cultures were confluent, medium was replaced with LTC medium.

Isolation of Hematopoietic CD34+ cells: Umbilical cord blood (CB), BM and peripheral blood samples were taken under sterile conditions and fractionated on Ficoll-Hypaque and buoyant (<1.077 gr/cm$^3$) mononuclear cells collected. The Cells were incubated with anti-CD34 antibodies and isolated by midi MACS (Milteny Biotech).

Isolation of endothelial cells: Endothelial culture cells were collected from peripheral blood. Buffy coat mononuclear cells from 50 or 100 ml of blood were resuspended in EGM-2 medium (Clonetics Inc, USA) without further cell subpopulation enrichment procedures and placed into plates coated with type I collagen (Becton Dickinson, USA). The plate was incubated at 37° C. in a humidified environment with 5% CO2. Culture medium was changed daily. After 24 hours, unattached cells and debris were removed by washing with medium. This procedure leaves the attached endothelial cells, as identified by morphology and staining with anti-endothelial monoclonal antibody P1H12, plus other mononuclear cells that died out within the first 2-3 weeks of culture.

The cells were kept at 37° C. in a tissue culture incubator under humidified condition with 5% CO$_2$. The medium was changed every 3 to 4 days. At 60-80% confluence, the cells were detached from the growth flask using 0.25% trypsin-EDTA and seeded into new flasks coated with 50 μg/mL of fibronectin (Sigma) as substrate.

MSCs-HSCs co-cultures: Isolated, CB derived CD34+ cells were seeded at equivalent numbers (about 5×10$^5$) onto monolayer or bioreactor containing equivalent densities of confluent MSCs. Upon addition to the bioreactor, medium flow was stopped for 0.25-16 hours to enable contact with MSCs and was re-initiated at a rate of 0.1-1.0 ml per minute. CD34+ cell seeded-MSCs carriers were removed for control studies in the absence of medium exchange. Co-cultures were maintained in growth medium, with or without cytokines. At various times (up to 4 weeks), nonadherent cells were collected from monolayer supernatants or from circulating culture medium via a container ([8], FIG. 1). Adherent cells were collected via sequential trypsinization and exposure to EDTA-based dissociation buffer (GIBCO BRL), followed by gentle pipetting of the cells. To avoid the presence of MSCs in the resulting suspension, the cells were resuspended in HBSS+10% FCS and were subjected to a 60 minutes adhesion procedure in plastic tissue culture dishes (Corning), at 37° C.

Osteogenic culture differentiation: Final bone tissue formation is executed in osteogenic culture differentiation medium composed of one or more of the following molecules in preferred concentration: dexamethasone (10-200 nM) (Sigma), sodium β-glycerophosphate (5-25 mM) (Sigma), 1,25 dihydroxycholecalciferol (calcitriol: 5-50 nM) (Sigma) and L-ascorbic acid-2-phosphate (10-500 nM) (Sigma).

Chondrocyte differentiation: Mesenchymal cells were seeded in concentration of 2*105 cells/tube—cells suspended in 1 ml medium with chondtogenic cocktail: DMEM HG, BMP-6 [500 ng/ml] (Sigma), TGF-b3 [10 ng/ml] (Sigma), ITS+premix [dil. :20 of the dil. Stock(:100)] (Sigma), Dexamethasone [100 nM] (Sigma), L-ascorbic acid 2-phosphate [50 mg/ml] (Sigma), Sodium pyruvate [100 mg/ml] (Sigma), Proline [40 mg/ml] (Sigma), Pen/Strep/Nys 1%, Glutamine 1%. The medium should be replaced every 2 days, for 21 days. After 21 days of differentiation, the culture was stained with Alcian blue (Sigma). Staining procedure: Fixation—formalin fixed, paraffin embedded tissue sections. Deparaffinize slides and hydrate to distilled water. Stain in alcian blue solution for 30 minutes. Wash in water. Counterstain in nuclear fast red solution for 5 minutes. Dehydrate through 95% alcohol, 2 changes of absolute alcohol, 3 minutes each.

Example 1: Growth of MSC and Osteoblasts 3-D Cultures in Flow System

Example 1 describes typical expansion experiments for co-culturing of these components, but with addition of the components at separate times.

In one experiment 30000 BM-derived MSCs were seeded on each carrier and the system was cultivated for 50 days. Results are shown in FIG. 2A. During the first six weeks, no cell expansion was noted but the following week was characterized by extensive cell proliferation. At the end of the 50-day period, expansion was measured at 2.8 folds (total of 85000 cells/carrier). 10000 CB derived CD34+ cells were then seeded onto the system of which early HSC (CD34+38-45+) counted for only 2500 cells (ratio of MSCs to HSC at time of co-culture establishment). Fourteen days later, at the time of harvest, MSCs cells were shown to expand by additional factor of 2. During the same period of time, HSC number in this system was increased by 42 folds.

In the second experiment, 42000 BM-derived MSCs were seeded on each carrier. Results are shown in FIG. 2B. An initial drop of stroma count was seen, that persisted for 24 days. 9400 CD34+ cells were then seeded on each carrier and culture allowed proceeding for additional 13 days. At the end of this period there was a net increase of 20% in the number of MSCs whereas HSC expanded by 90%.

These results show that by varying the initial expansion period of stroma mono-culture and the ratio of seeded CD34+ to MSCs at time of establishment of the co-culture system, a control over final cell blend could be attained. This is a desired ability where demands for strength and elasticity of bone material could vary.

FIG. 3 shows Scanning Electron Microscope (SEM) and confocal micrographs of 3-D synthetic scaffold seeded with MSCs in cultured in static and in dynamic flow system:

(A) SEM micrograph of human MSCs seeded on 3D scaffold;

(B) Confocal image of human MSCs seeded on 3D scaffold. Numerous elongated cells are seen throughout the scaffold. Note auto fluorescence of the scaffold fibers (green: Confocal image of static culture ×10).

(C) SEM of scaffold cultured with human MSCs in dynamic flow growth system. Note, dense cell distribution and extra cellular matrix as well as distinct 3-D meshed structure of the scaffold containing cells which are aligned along and between the fibers.

(D) Confocal microscope projection image of human MSCs cultured on 3-D scaffold construct in dynamic flow system. Numerous elongated cells are seen throughout the scaffold. Note cell cytoplasm (blue) and nuclei (red).

FIG. 4 shows light microscopy images of the scaffold containing mesenchymal cells after in vivo subcutaneous implanting in nude mouse:

(A) The implant appears to be fully integrated with the surrounding tissues. Dense cell distribution and matrix containing infiltrated blood vessels (arrows) are observed.

(B) A higher magnification of the previous figure showing cells attachment to the nanofibers and blood vessels containing erythrocytes within the scaffold (arrows).

Example 2: MSC Differentiation to Osteoblasts

This Example relates to 2D and 3D cultures of MSC cells which are then differentiated into preosteoblasts and osteoblasts. The 3D culture is similar to Example 1, except that the component cells are placed together simultaneously in culture.

Final bone tissue formation is executed in osteogenic culture differentiation medium composed of one or more of the following molecules in preferred concentration: dexamethasone (10-200 nM) (Sigma), sodium β-glycerophosphate (5-25 mM) (Sigma), 1,25 dihydroxycholecalciferol (calcitriol: 5-50 nM) (Sigma) and L-ascorbic acid-2-phosphate (10-500 uM) (Sigma).

Figure 5:
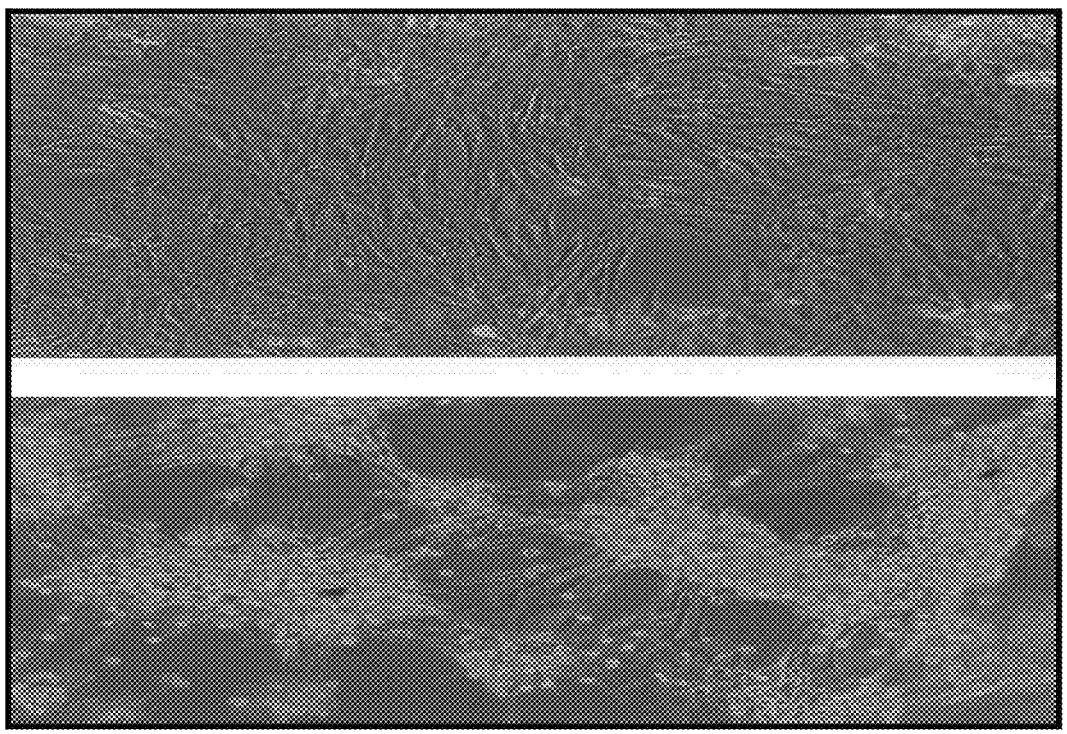
FIG. 5 shows light microscopy image of MSC cultures, 7 days after inducing differentiation to osteoblasts.

FIG. 5 shows light microscopy image of MSC cultures, 7 days after inducing differentiation to osteoblasts.

Figure 6:
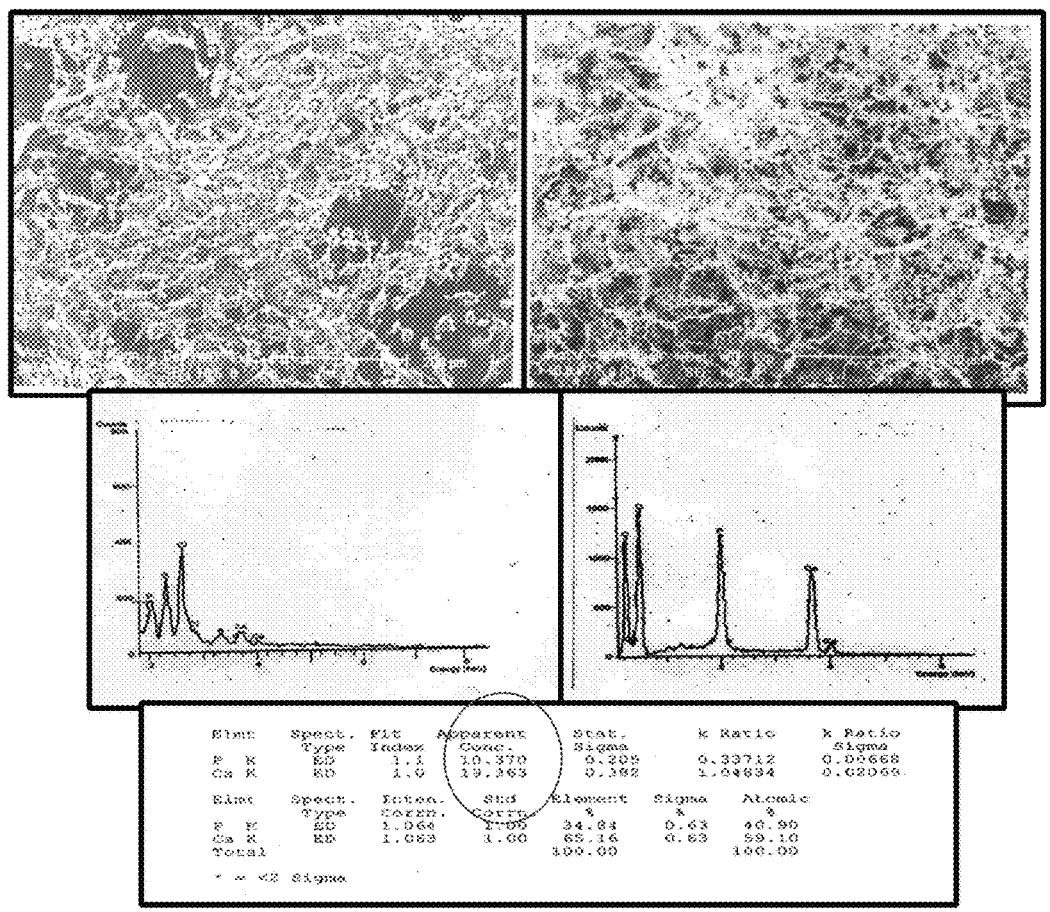
FIG. 6 shows MSC differentiation to osteoblasts, and EDS spectrum analysis of elements in molar concentration in MSCs cultures after 3 weeks.

FIG. 6 shows MSC differentiation to preosteoblasts and osteoblasts, and EDS spectrum analysis of elements in molar concentration in MSCs cultures after 3 growth weeks.

Example 3: Co-Culture of Osteoprogenitor Cells and Endothelial Cells

Osteoprogenitor cells (OS) and Endothelial cells (C) were co-cultured on a 3-D scaffold for inducing osteogenesis in vitro.

Bone marrow MSCs—derived osteoprogenitor cells (OS) (50,000 cells/well of 24 wells culture plate) were either plated alone or co-cultured with Endothelial cells (EC) (2,000 cells/well of 24 wells culture plate), on 3-D hydrogel scaffold in α-MEM medium containing osteogenic supplements, for up to 21 days. Endothelial cells were similarly cultured alone.

The effect of endothelial cells on the differentiation pattern of osteoprogenitor cells to the osteogenic lineage was followed by Alizarin Red S, staining for demonstration of calcium deposits and by osteocalcin inmmunostaining for demonstrating the synthesis of bone specific macromolecules.

Figure 7:
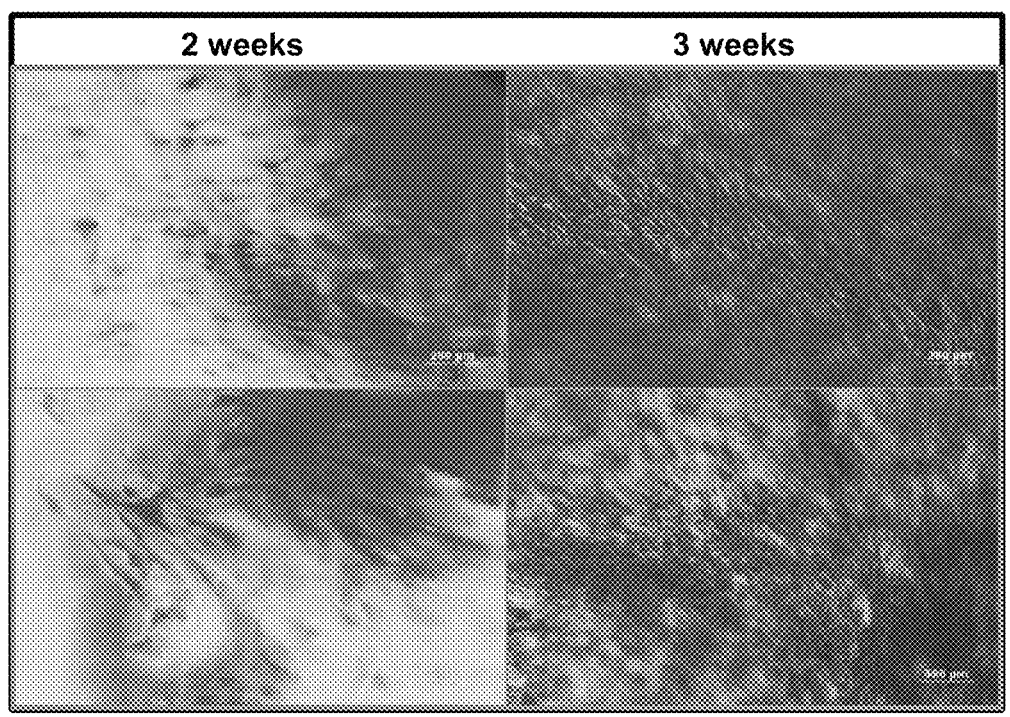
FIG. 7 shows a microscopic view of a co-culture containing two cell types (osteoprogenitor cells and endothelial cells) after 7 and 14 days in culture.
Figure 8:
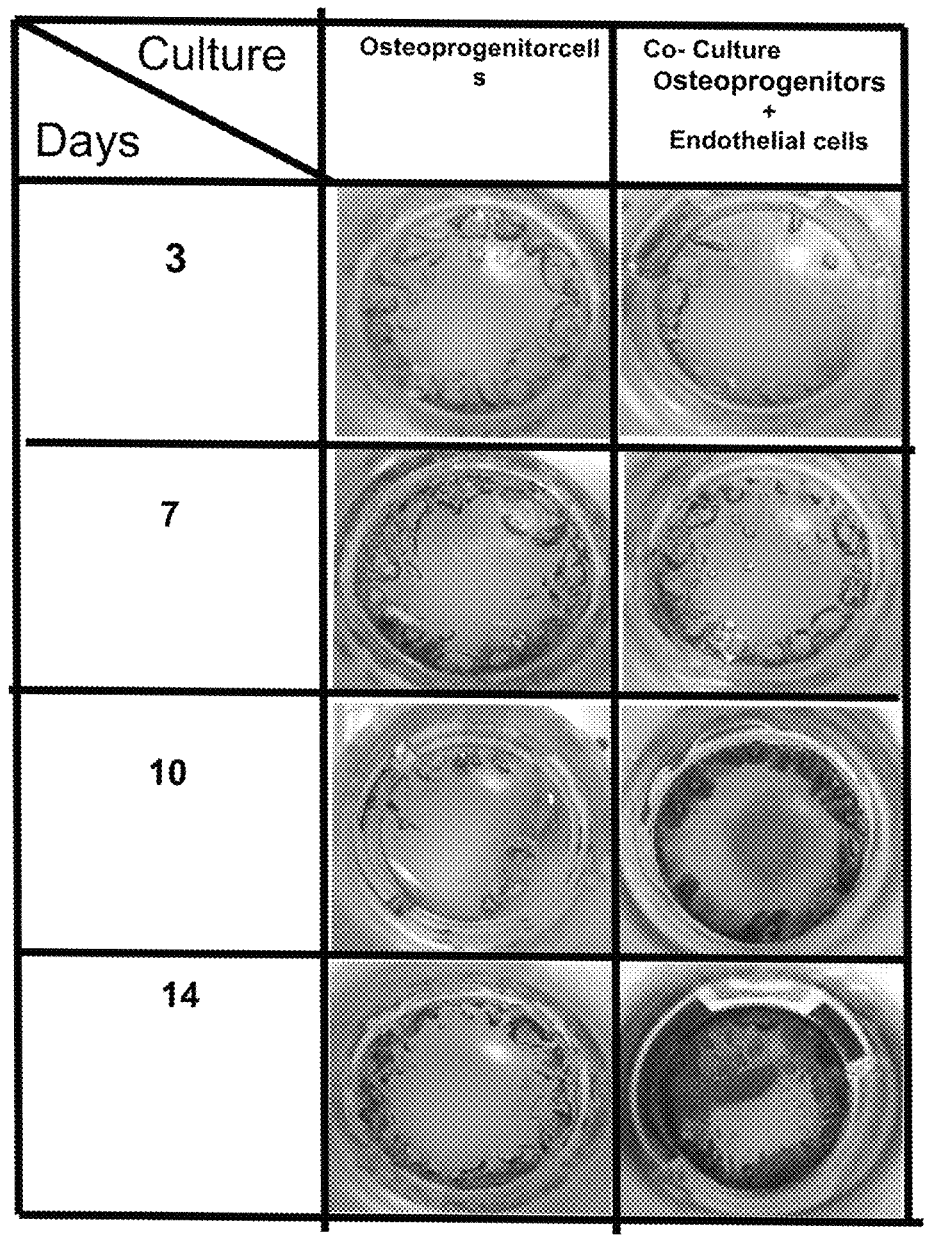
FIG. 8 shows Alizarin red staining in co-cultures containing two cell types (osteoprogenitor cells and endothelial cells); demonstrate those cells 3-D interaction
Figure 9:
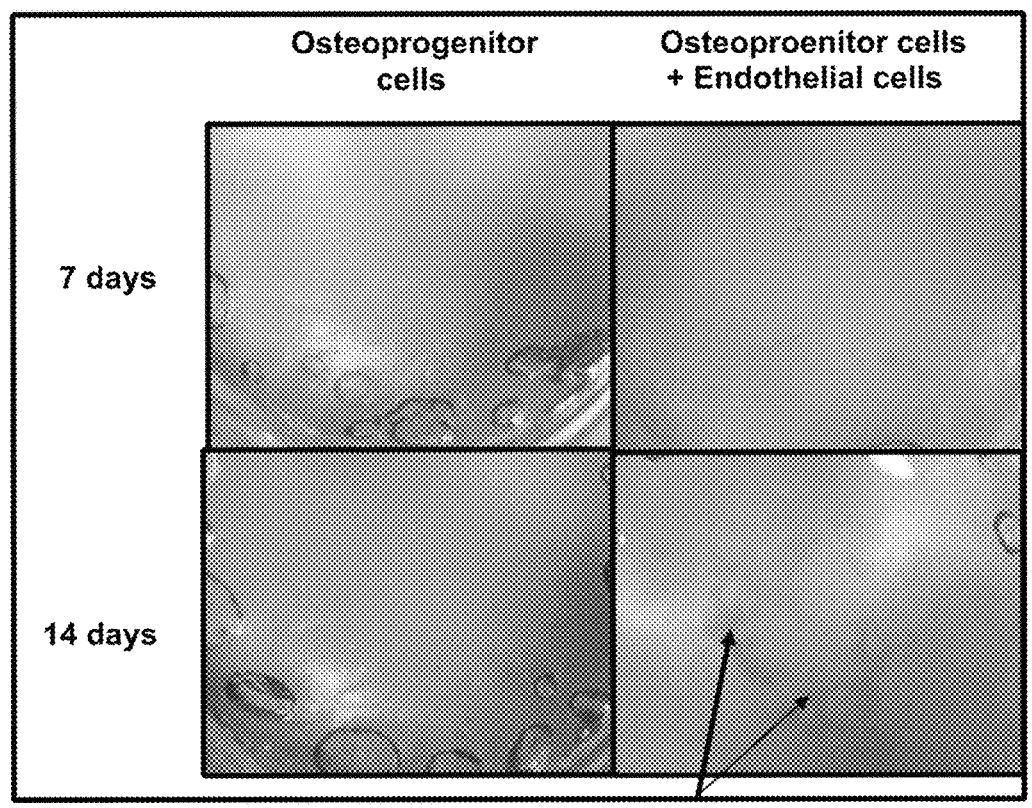
FIG. 9 shows that positive immunostaining for osteocalcin was higher in co-cultures of osteoprogenitors and endothelial cells after 14 days in culture.

The results in FIG. 7-9 demonstrate the difference in proliferative activity of these two cell types. Thus when cultured alone, the osteoprogenitor cells proliferated at a lower rate than the endothelial cells. In addition, those results prove that the osteogenic differentiation progressed only when a high number of cells (close to confluence) were present in the culture system. Thus, as compare to the endothelial cells, a higher number of osteoprogenitors was needed for the culture.

In order to be able to co-culture these two cell types together, two approaches were used:

A: The osteoprogenitor cells were cultured from the beginning at a larger numbers (50,000 cells/group) and the endothelial cells were plated at lower numbers (2,000 cells/group).

B: The osteoprogenitor cells were seeded first and only after 7 days (when their numbers increased) the endothelial cells were added to the culture. This approach was crucial in the 3-D micro sphere dynamic culture technique, since the osteoprogenitor cells formed bridges between the micro spheres and caused their coalescence forming a clot, prior to the seeding of the endothelial cells (for additional week)

FIG. 7 shows a microscopic view of a 3-D co-culture containing both cell types (osteoprogenitor cells and endothelial cells) after 7 and 14 days in culture demonstrating that cell quantity increased in the culture from 7 to 14 days.

Osteoprogenitor cells and endothelial cells were co-cultured for 3, 7, 10, 14 days on 3-D hydrogel scaffold, stained with Alizarin Red S staining, for calcium deposits.

As shown in FIG. 8, the combination of osteoprogenitor cells and endothelial cells caused induction of Alizarin Red S staining in cultures containing both cell types after 14 and 21 days, as compared to control cultures with osteoprogenitor cells only. This result indicates induced calcium deposition in the 3-D co-culture combination. Note gradual increase of alizarin red staining in co-culture after 10 and 14 days. Osteoprogenitor cells and endothelial cells were co-cultured for 7 and 14 days on hydrogel scaffold.

FIG. 9 shows that positive immunostaining for osteocalcin was higher in co-cultures of osteoprogenitors and endothelial cells after 14 days in culture, which indicates synthesis of bone-specific macromolecule. Note staining after 14 days in culture (indicated by arrows)

The results shown in FIGS. 8 and 9 indicate that the 3-D combination of the two cell types enhanced calcium deposition, indicating enhanced osteogenic differentiation including mineralization, by alizarin red S, and promoted synthesis of bone specific, osteocalcin positive macromolecules.

Example 4: Growing 3-D Co-Culture of Osteoprogenitor Cells and Endothelial Cells Osteoprogenitor cells (OS) and Endothelial cells (C) were co-cultured on 3-D hydrogel scaffold for inducing osteogenesis in vitro.

Bone marrow MSCs derived osteoprogenitor cells (OS) were plated in co-cultured with Endothelial cells (EC), on 3-D scaffold in α-MEM medium containing osteogenic supplements, for up to 21 days.

Cell viability was followed by live/dead fluorescent markers. The osteoprogenitor cells were pre labeled with CFDA (green fluorescence), and the endothelial cells were pre labeled with Hoecht (blue fluorescence). Osteoprogenitor cells (50,000 cells/construct) were first seeded on micro sphere hydrogel scaffold in dynamic culture for up to 7 days (FIG. 10), followed by seeding the endothelial cells (2,000 cells/construct) for additional 7 days.

Cells cultured on the 3-D hydrogel scaffold were stained with a cell tracer reagent: Carboxyfluorescein Diacetate Succinimidyl Ester (CFDA SE). The non-fluorescent CFDA SE diffuses into the cells and upon cleavage by intracellular esterases become fluorescent indicating viable proliferating cells. Hoecht stain penetrates to the cell nuclei and enables detection of viable cells in the culture.

Figure 10:
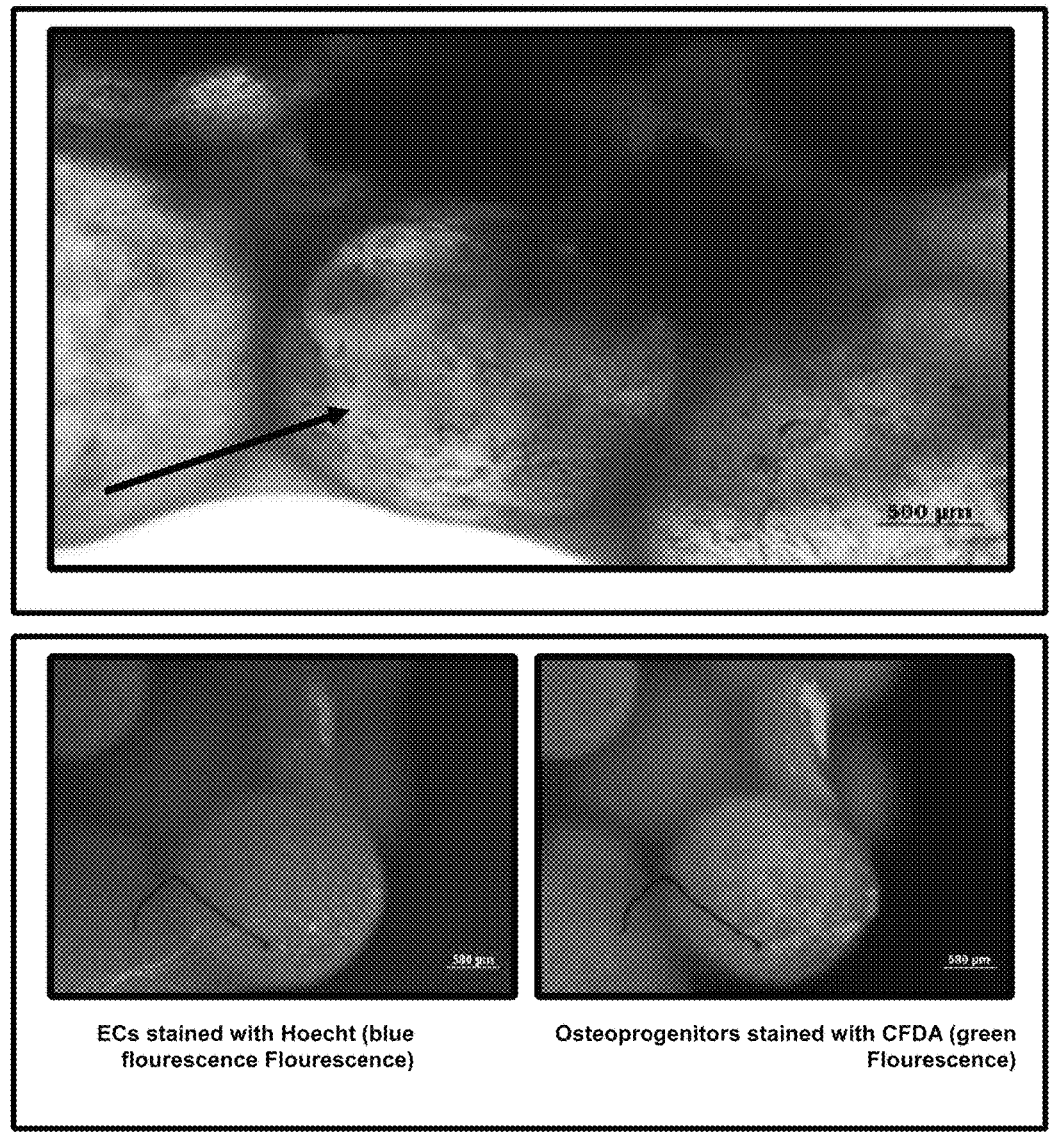
FIG. 10 shows a general view of micro sphere construct loaded with osteoprogenitor and endothelial cells before and after seeding; the co-culture of Osteoprogenitor cell (CFDA, green) and Endothelial cells (Hoecht, blue) cultured on microspheres construct; demonstrating the co-localization of both endothelial cells and osteoprogenitors seeded on the micro sphere scaffold.

FIG. 10 demonstrate a general view of the 3-D micro spheres construct loaded with osteoprogenitor and endothelial cells. The two cell populations, the osteoprogenitors and the endothelial cells, were viable on the scaffold and can be used for the in vivo implants. The scaffold microspheres were first seeded with osteoprogenitor cells (pre-labeled with CFDA, green) and than were seeded with ECS (pre-labeled with Hoecht, Blue). FIG. 10 also shows the interaction between the co-culture of Osteoprogenitor cell (CFDA, green) and Endothelial cells (Hoecht, blue) cultured on the microspheres construct (1 week; dynamic culture) demonstrating the high density of viable osteoprogenitor and endothelial cells and the co-localization of both endothelial cells and osteoprogenitors seeded on the on the micro sphere scaffold, (overlap of the green and blue colors).

Example 5: Growing 3-D Co-Culture of Osteoblasts and Chondrocytes

One of the first needs for bone cartilage grafts is injuries to the cartilage of the knee joint. Injuries to the knee are not uncommon among both professional athletes as well as active non-professional sports enthusiasts; and incidents of knee trauma are also among the unfortunate results caused by accidents of all sorts. There is a large group of patients in need of a solution to damaged knee cartilage.

Allograft transplantation is a conventional method for treating such injuries. The advantages of allograft transplantation include good results for a longer time period post surgery and the fact this treatment can be applied to a wider spectrum of patients. However, the lack of donors and the unavailability of these grafts, the necessary viability of the chondrocytes and osteoblasts, as well as the safety issue regarding the supplied donor tissue and the need for matching the site-specific requirements (size, shape, cartilage thickness), limit the use of those tissues.

Using bone cartilage replacement prosthetics and growing cellular-based bone cartilage implants in vitro may allow the creation of osteoarticular grafts, which comprise implant consisting of hyaline cartilage attached to bone. This complex graft can be grown in vitro, kept frozen and stored for indefinite periods of time. The cartilage bone graft received following thawing contains a high level of viable chondrocytes. This approach will allow the growth and supply of match, safe and available tissue. The ability to grow and cryopreserve cartilage grafts also provides a way to store the in vitro created tissues for long term, thereby creating a bank of various shapes, sizes and other specific characteristics including donor age, cartilage thickness, etc. Cellular-based bone cartilage implants may supply safer tissue for transplantation, reduce the waiting time for an appropriate donor and allow better matching of tissue shape and size for better repair success.

In order to achieve this goal, 3-D osteochondral allograft plugs, made of osteogenic implants are treated on one side to induce the growth of cartilage tissue. The final growth phase on the side of the plug is stimulated toward chondrocytes differentiation using growth factor such as, but not limited to, TGF-beta (Sigma) BMPs (Sigma), retinoids (Sigma), FGFs (Sigma), GH (Sigma), IGFs (Sigma) and transferrin (Sigma). Following the cartilage growth, the allograft plugs are processed, cryopreserved and store ready for use. When needed, the plugs are thawed in the operating theatre prior to transplantation and transplanted using a press fit technique.

Figure 11:
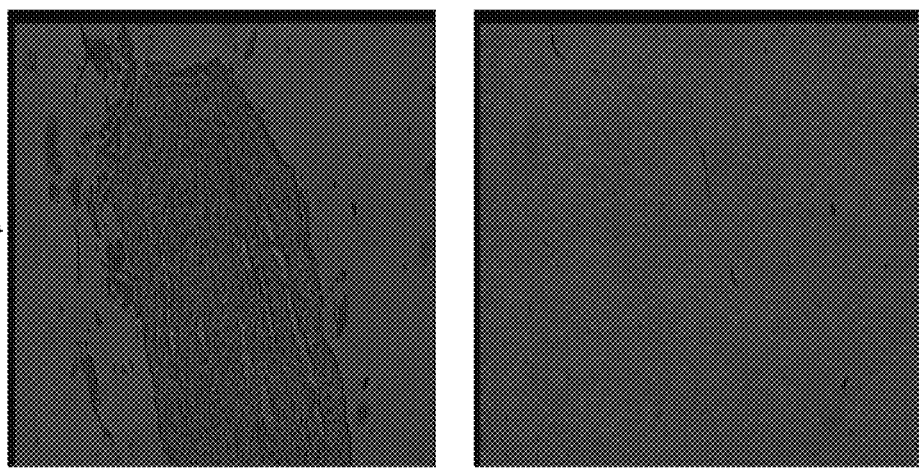
FIG. 11 shows the mesenchymal stromal cells ability to different in vitro into chondrocytes.

FIG. 11 demonstrates the ability of ex vivo expanded 3-D mesenchymal cells to differentiate in vitro into mature chondrocytes.

Example 6: Transplanting 3-D Co-Culture of Osteoprogenitor Cells and Endothelial Cells In order to further increase the osteogenic potential of scaffold-based implants, a cell-therapy approach was used to incorporate osteoprogenitor cell-derived from bone marrow Mesenchymal Stromal cells (MSCs) into the scaffold to enhance bone repair. Osteoprogenitor cells (OS) and Endothelial cells (EC) were co-cultured on the 3-D scaffolds in vitro. The results presented in FIGS. 12-16 were validated by the use of specific osteogenic markers demonstrating that cultures of sufficient numbers of osteogenic cells, endothelial cells and growth factors could conceivably be used with scaffolds for bone tissue engineering to repairing bone loss in aging and in bone transplantation (FIG. 15).

The present inventors have demonstrated that the methods used for the in vitro selection of the osteogenic subpopulation from MSCs cultures and the methods used to incorporate them in scaffold are crucial for successful transplants for future use in tissue engineering bone repair. The present inventors have also demonstrated that the scaffold is preferably biocompatible for selected osteogenic cells and provides support for proliferation and differentiation.

The scaffold is optionally and preferably biocompatible, osteoconductive, biodegradable and osteoinductive, but not immunoreactive. The 3-D scaffolds provide the necessary support for cells to proliferate and maintain their capacity to differentiate.

Transition from a 2-D culture system to the 3-D scaffold provides a system that imitates the natural 3-D structure of the body tissues and specifically the structure of bone. The 3-D scaffolds containing MSC-derived osteoprogenitors and additional supporting cells can be employed within transplants in order to enhance bone repair. The complex construct is intended to mimic the native in vivo microenvironment and this necessitates construction of bioactive scaffolds which are also capable of supporting vascularization as well as cell proliferation and osteogenic differentiation.

Preclinical animal tests developed by the present inventors are a crucial step prior to conduction of the actual clinical trials and finalized the preclinical tests aimed to validate the functionality of the transplanted cells, its safety parameters and the assessment of non-immunoreactivity of either the cells or the scaffold in the designed transplanted cell-scaffold constructs. The described in vivo animal tests constitute a step midway between the in vitro studies and the human clinical applications, and are crucial for demonstrating the functionality of the designed cell-scaffold constructs.

Figure 12:
FIG. 12 shows the in vivo critical size defect experimental model and the ability to create a non healing bone defect.
Figure 12:
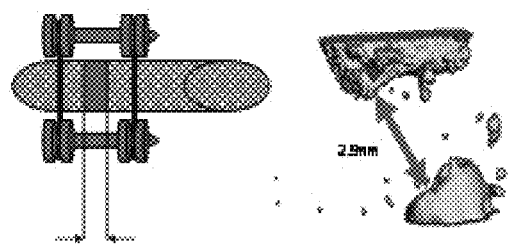
Figure 12:
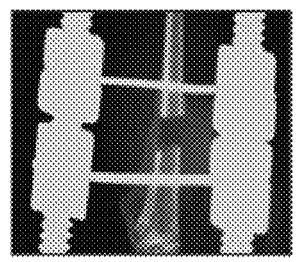

FIG. 12 demonstrates the small animal model developed and used by the present inventors in the small animal (mice and rats) preclinical studies. The available methods include the use of an external fixation device for conducting a critical size defect (CSD) in long bone that will not heal. As FIG. 12 demonstrates, following the creation of critical defect and bone external fixation, the bone defect does not heal for more than 3 months.

Figure 13:
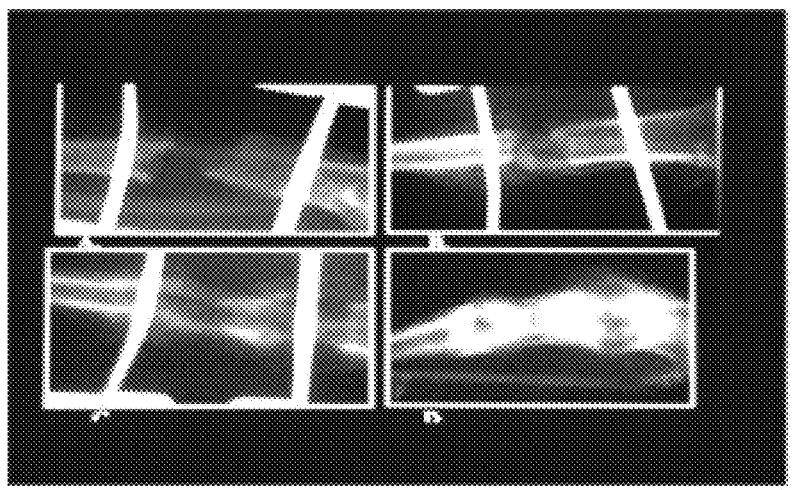
FIGS. 13 and 14 show the preclinical results based on using the in vivo Critical size defect and demonstrating the 3-D multi cells culture ability to heal a non healing bone defect.
Figure 14:
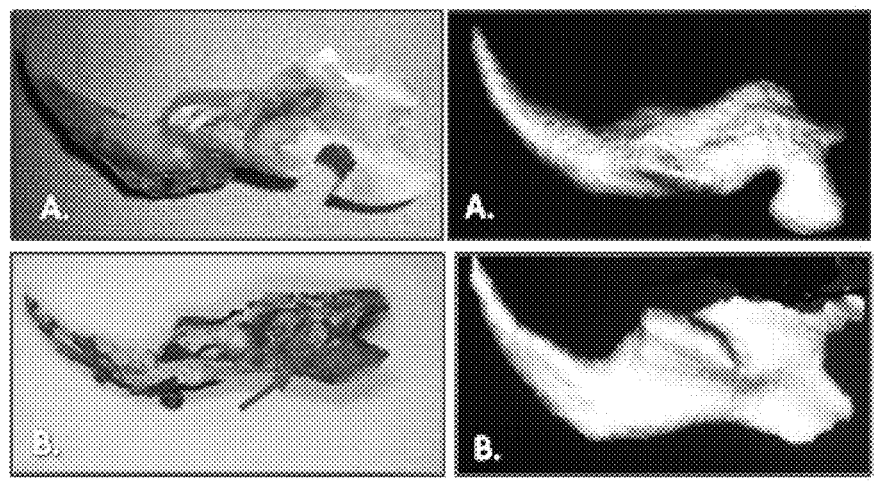
Figure 15:
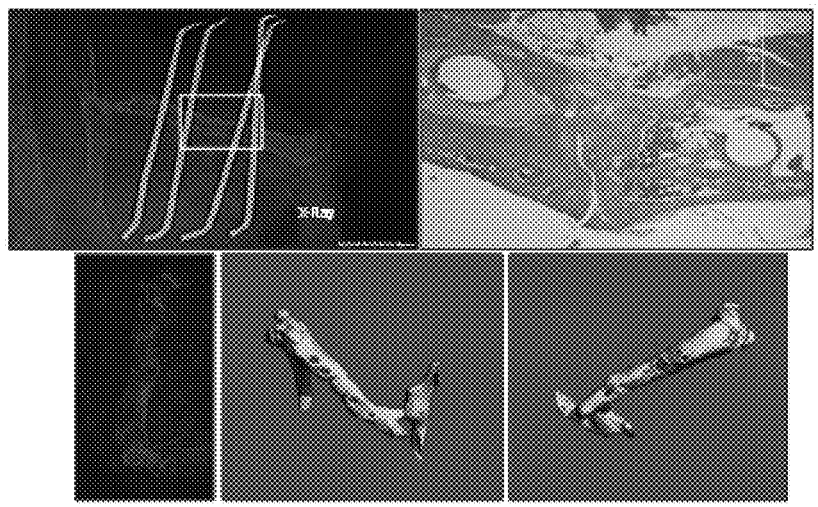
FIG. 15 show the preclinical results demonstrating the biodegradable artificial bone transplanted within this in vivo model to be accepted by the recipient and to allow the development of complete organ including blood vessels.

FIGS. 13-14 demonstrate other critical gap animal models used by the present inventors for studying bone repair, including bone segmental defects conducted in rat tibia and the three-wall bone defect conducted in rat mandible. Both models tested by the present inventors have demonstrated successful and complete bone repair within 6 weeks following the new in vitro developed bone transplant.

Figure 16:
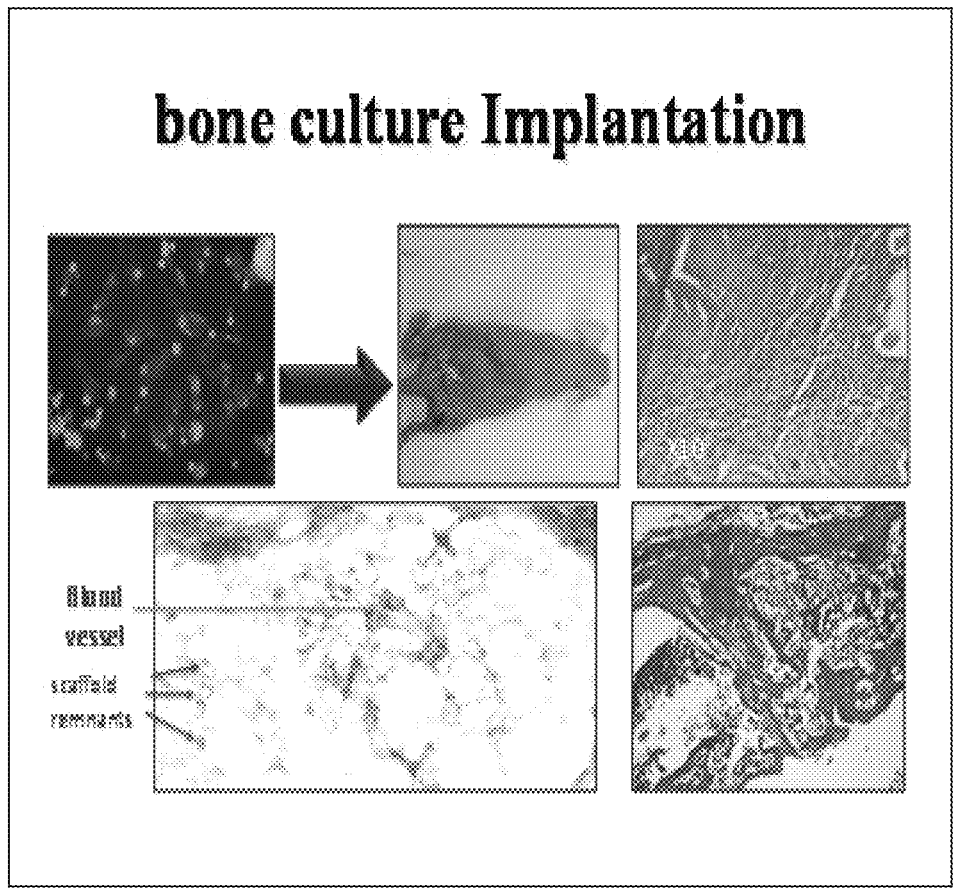
FIG. 16 demonstrates cell-scaffold constructs of GFP labeled MSCs cultured in 3D scaffolds.

FIGS. 15-16 demonstrate the use of immunodeficient mice strains (Nude, SCID/NOD) for testing human cells transplanted. The mice were treated by bone implant transplants (orthoptopic animal model). FIG. 15 demonstrates full repair of the defect as shown by x-ray, histology and µCT. FIG. 16 demonstrates cell-scaffold constructs of GFP labeled MSCs cultured in 3D scaffolds and transplanted subcutaneously/intramuscularly (ectopic animal models), revealing new bone formation and the formation of blood vessels in the transplant animal.

Example 7: Critical Gap Bone Repair Model Test In Vivo

The present invention, in at least some embodiments, is generally concerned with creation of critical size defects (CSD) in bones of animals, including humans, using external bone fixators.

In accordance with one aspect of the present invention, there is provided an external fixation system for creating a CSD in a long bone of an animal, the system comprising a frame composed of at least two pins for percutaneous insertion from the lateral to the medial side of said bone spaced apart in a distance greater than the length of the CSD; and at least one moldable bridge for fixation of said pins with respect to each other and over said bone in a manner to prevent the pins from any longitudinal or rotational displacement with respect to said bone and with respect to each other.

The pins are inserted perpendicular or with a certain angle with respect to the long axis of the bone and are adapted to be long enough to protrude beyond the opposite cortices thereof. In this case two moldable bridges are used for fixation at both the lateral and the medial sides of the bone.

Any one or more of the following features may be included in the system according to the present invention. For example, the system may further comprise 4 pins, two of them positioned at the upper third of the bone, and the other two are positioned at the lower third of the bone, having a CSD there between. In this case the system may further comprise more than one bridge, each bridge fixating one couple of pins (one pin from the upper third of the bone and another pin from the lower third of the bone).

Each couple of pins may be inserted perpendicular or with a certain angle with respect to the long axis of the bone. The system may comprise any even or odd number of pins. The bridge may be made of fast hardening acrylic materials, such as dental acrylic paste. The system is suitable for small animals such as mice, as well for larger animals such as horses, cows, bulls and other agriculturally important animals, or even humans.

According to a further aspect of the present invention, there is provided a kit, the kit comprising the external fixation system for creation of a CSD in a long bone of an animal, the system comprising a frame composed of at least two pins for percutaneous insertion from the lateral to the medial side of said bone spaced apart in a distance greater than the length of the CSD; and at least one moldable bridge for fixation of said pins with respect to each other and over said bone in a manner to prevent the pins from any longitudinal or rotational displacement with respect to said bone and with respect to each other; and a mold made of flexible material for temporarily positioning and fixation of a limb of the animal to allow a desired position thereof. The mold is soft and may be made of semi-rigid silicon.

According to a further aspect of the present invention, there is provided a method for creation of a critical size defect (CSD) in a long bone of an animal, the method comprising: providing an external fixation system comprising a frame composed of at least two pins and a at least one moldable bridge; temporarily positioning and fixation of a limb with a flexible mold of the animal to allow a desired position thereof, in which there is no damage occurs to the blood vessels and nerves of the animal's limb; percutaneous insertion of said pins from the lateral to the medial side of said bone in a distance greater than the length of the CSD; fixation of said pins with said moldable bridge with respect to each other and over said bone in a manner to prevent the pins from any longitudinal or rotational displacement with respect to said bone; and induction of the CSD.

In case that two moldable bridges are used for fixation at both the lateral and the medial sides of the bone, as described above, the mold is removed before the fixation of the pins at the medial side of the bone.

In addition to creating a CSD, the method according to the present invention may be used for creating of fractures, partial fractures and immobilizations of the animal bones and joints (between femur and tibia).

Although the below detailed example centers around mice as a test model animal, in fact the system and method may be adapted for any larger animal by one of ordinary skill in the art.

Figure 17:
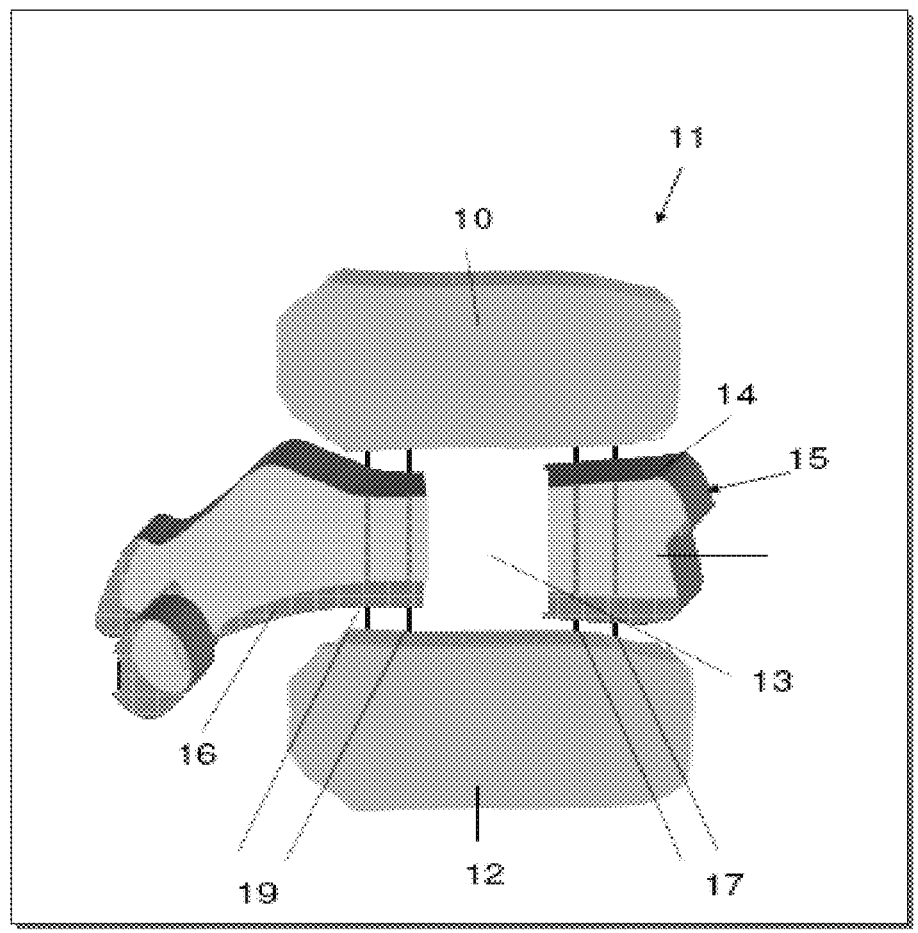
FIG. 17 is a front view of an external fixation system according to the present invention.

FIG. 17 illustrates an external fixation system generally designated 110 for creating a critical size defect (CSD) 130 in a long bone 150 of an animal (not shown), having a lateral side 140 and a medial side 160. The system is designated for use with small animals, but is adapted to be used with large animals as well. The system comprising a first couple of pins 170 and a second couple of pins 190, protruding from both the lateral 140 and the medial 160 sides of the bone 150, positioned in parallel relation at the right and the left sides of the CSD 130. The first and the second couples of pins 170 and 190 are spaced apart at a distance greater than the length of the CSD. The pins 170 and 190 are fixated over the bone 150 and with respect to each other with a lateral moldable bridge 100 and a medial moldable bridge 120, so as to prevent them from any longitudinal or rotational movement with respect to the bone 150 and with respect to each other. The moldable bridges 100 and 120 may be made of fast hardening acrylic materials, such as acrylic dental paste, and together with the pins they create a frame having a weight of no more than 1 gr.

FIGS. 18 to 21 schematically illustrate a process of a creation of the CSD in a femur of a mouse 27.

Figure 18A:
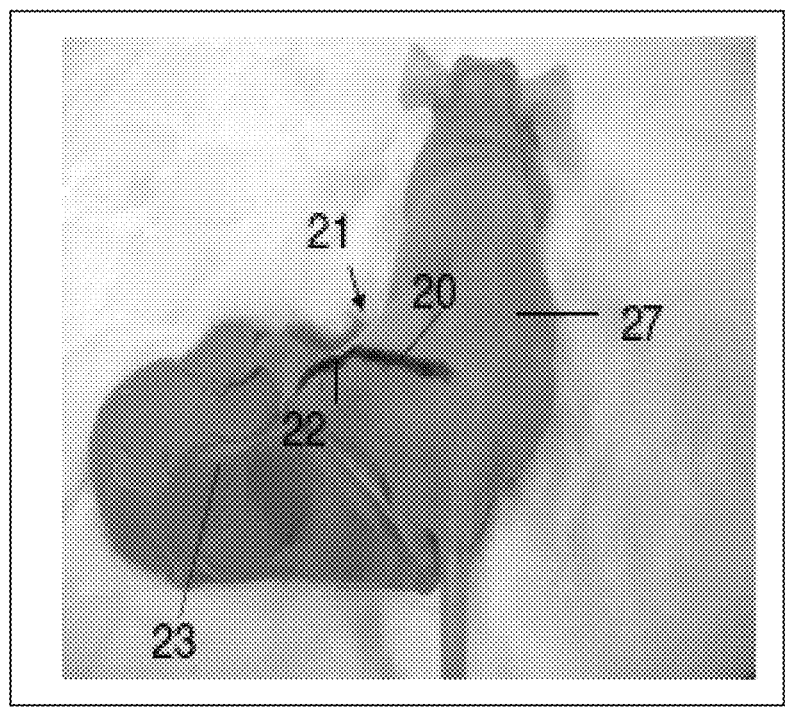
FIG. 18A illustrates a temporal positioning and fixation of a limb of a mouse.
Figure 18B:
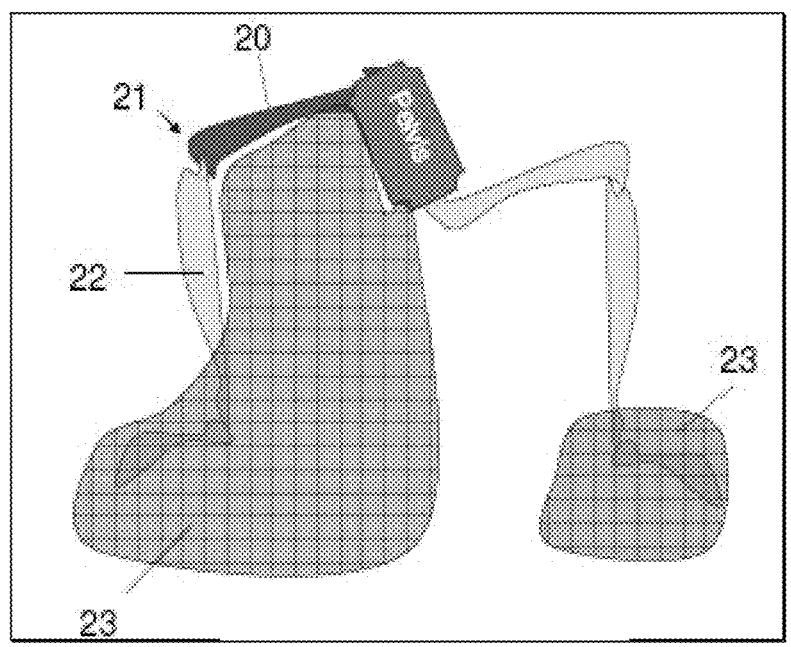

FIGS. 18A and 18B demonstrate the first stage of the process. This stage is temporal positioning and fixation of the limb 21 (comprising of the femur 20 and the tibia 22) of the mouse with a semi-rigid silicon mold 23. The mold 23 is soft and hardens slowly, thereby maintaining the limb 21 in a desired position.

Figure 19:
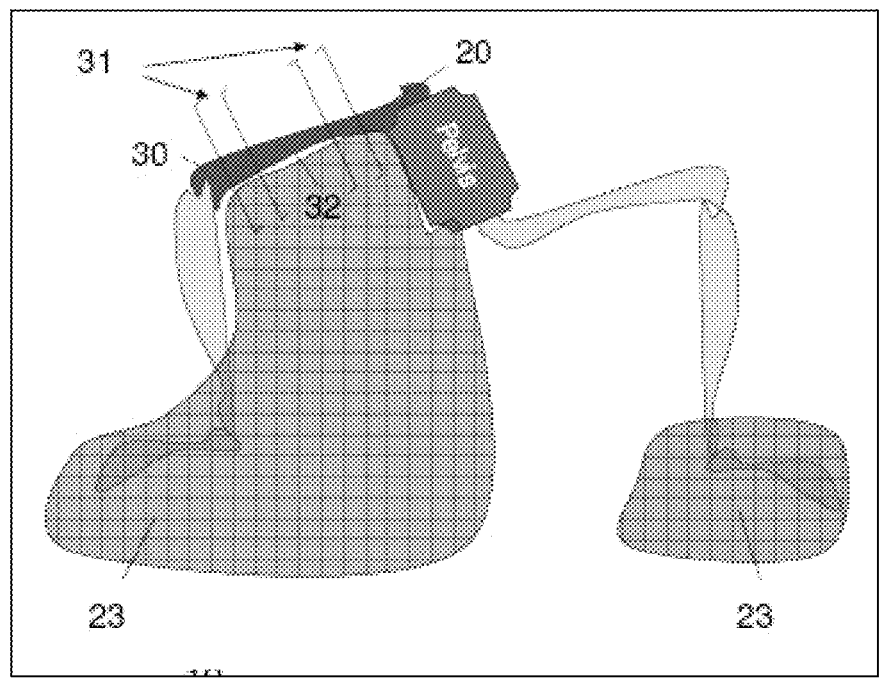

FIG. 19 demonstrates the second stage of the process. This stage is percutaneous insertion of pins 31 (e.g. commercial needles 25G) from the lateral side 30 to the medial side 32 of the femur 20 through holes (not shown that were manually drilled by a drill of corresponding diameter (0.3 mm) from each side of the femur 20. After the insertion of the pins 31, they are first fixated with the lateral moldable bridge 100 at the lateral side 30 of the femur 20. Then, the silicon mold 23 is removed and the pins are fixated with the medial moldable bridge 120 at the medial side 32 of the femur 20.

Figure 20:
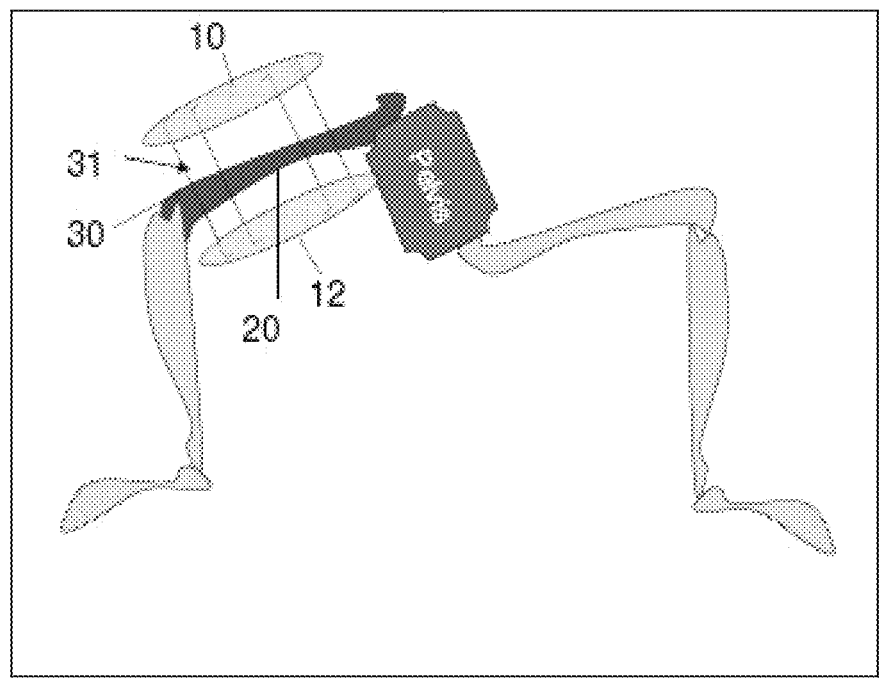

FIG. 20 demonstrates the third stage of the process wherein the pins 31 are already fixated with both moldable bridges 100 and 120 and the silicon mold 23 is removed.

Figure 21:
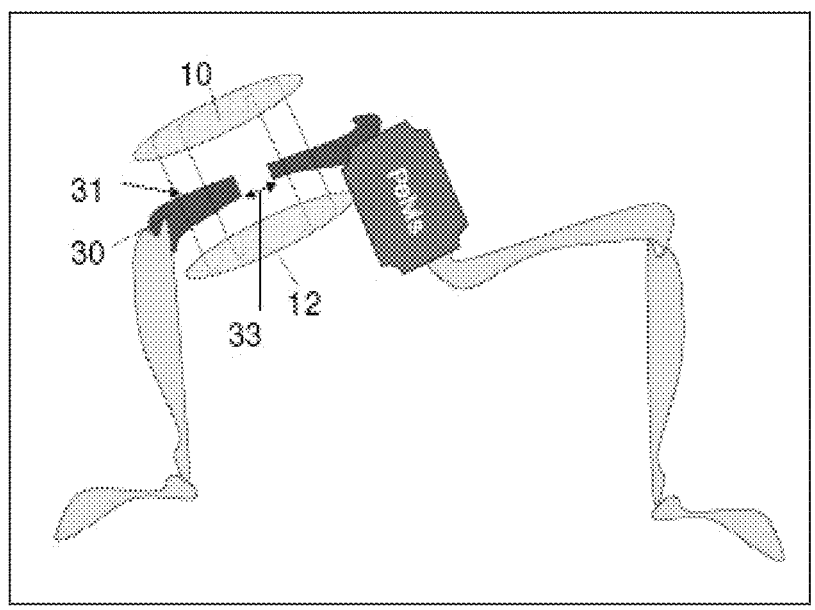
Figures 22A, 22B:
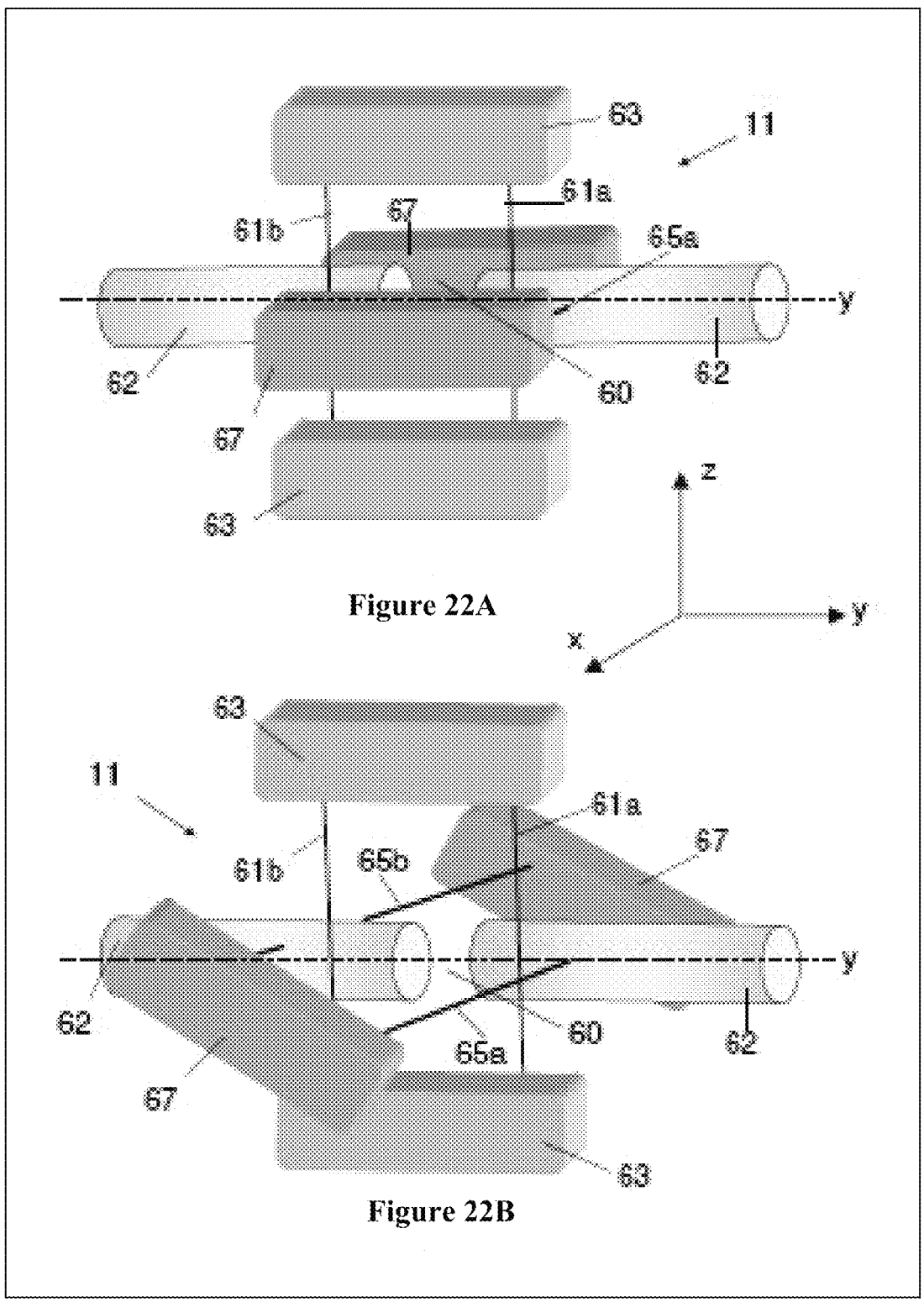
FIGS. 22A and 22B illustrate other embodiments of the external fixation system according to the present invention.

FIG. 21 demonstrates the last stage of the process is inducing the CSD. When the pins 31 are already fixed over the femur 20, the CSD 33 of about 2 mm is induced between the pins 31.

FIGS. 19 and 20 illustrate other embodiments of the external fixation system 110 for creating a CSD 60 in a long bone 62. The system 110 comprises a first couple of pins 61a and 61b fixated with first moldable bridges 63, and a second couple of pins 65a and 65b (shown in FIG. 19B) fixated with second moldable bridges 67. The pins 61a and 65a are positioned at the right side of the CSD 60, and the pins 61b and 65b are positioned at the left side of the CSD 60. As shown in FIG. 19A, the first couple of pins 61a and 61b is parallel to the z axis, so as the bridges 63 are parallel to the y axis (which is the long axis of the bone 62). The second couple of pins 65a and 65b is parallel to the x axis, so as the bridges 67 are parallel to the axis y of the bone. The couples of pins are not necessarily have to be parallel to one of the main axes x, y or z, as shown in FIG. 19B, in which the second couple of pins 65a and 65b is positioned in a certain angle with respect to the x-y plane.

After the fixation process is completed, the CSD of about 3.5 mm is induced between the pins using a drill motor.

It is appreciated that certain features of the invention, which are, for clarity, described in the context of separate embodiments, may also be provided in combination in a single embodiment. Conversely, various features of the invention, which are, for brevity, described in the context of a single embodiment, may also be provided separately or in any suitable subcombination or as suitable in any other described embodiment of the invention. Certain features described in the context of various embodiments are not to be considered essential features of those embodiments, unless the embodiment is inoperative without those elements.

Although the invention has been described in conjunction with specific embodiments thereof, it is evident that many alternatives, modifications and variations will be apparent to those skilled in the art. Accordingly, it is intended to embrace all such alternatives, modifications and variations that fall within the spirit and broad scope of the appended claims.

Citation or identification of any reference in this application shall not be construed as an admission that such reference is available as prior art to the present invention.

To the extent that section headings are used, they should not be construed as necessarily limiting.

REFERENCES

Aggarwal S, Pittenger M R 2005 Human mesenchymal stem cells modulate allogeneic immune cell responses. Blood. 105:1815-22.

Bielby R C, Boccaccini A R, Polak J M, Buttery L D. 2004 In vitro differentiation and in vivo mineralization of osteogenic cells derived from human embryonic stem cells. Tissue Eng. 10:1518-25.

Bruder S P, Kraus K H, Goldberg V M, Kadiyala S. 1998a The effect of implants loaded with autologous mesenchymal stem cells on the healing of canine segmental bone defects. J Bone Joint Surg Am. 80:985-96.

Bruder S P, Kurth A A, Shea M, Hayes W C, Jaiswal N, Kadiyala S. 1998b Bone regeneration by implantation of purified, culture-expanded human mesenchymal stem cells. J Orthop Res. 16:155-62.

Buttery L D, Bourne S, Xynos J D, Wood H, Hughes F J, Hughes S P, Episkopou V, Polak J M. 2001 Differentiation of osteoblasts and in vitro bone formation from murine embryonic stem cells. Tissue Eng. 7:89-99.

Chakrabarti S, Mautner V, Osman H, Collingham K E, Fegan C D, Klapper P E, Moss P A, Milligan D W. 2002 Adenovirus infections following allogeneic stem cell transplantation: incidence and outcome in relation to graft manipulation, immunosuppression, and immune recovery. Blood. 100:1619-27.

Cinotti G, Patti A M, Vulcano A, Della Rocca C, Polveroni G, Giannicola G, Postacchini F. 2004 Experimental posterolateral spinal fusion with porous ceramics and mesenchymal stem cells. J Bone Joint Surg Br. 86:135-42.

Choi K, Kennedy M, Kazarov A, Papadimitriou J C, Keller G. 1998 A common precursor for hematopoietic and endothelial cells. Development. 125:725-32.

Cohen Y, Nagler A. 2004 Umbilical cord blood transplantation—how, when and for whom? Blood Rev. 18:167-79.

Gang E J, Hong S H, Jeong J A, Hwang S H, Kim S W, Yang I H, Ahn C, Han H, Kim H. 2004 In vitro mesengenic potential of human umbilical cord blood-derived mesenchymal stem cells. Biochem Biophys Res Commun. 321:102-8.

Gerasimov IuV, Fridenshtein AIa, Chailakhian R K, Shishkova V V. 1986 Differentiation potentials of clonal strains of bone marrow fibroblasts. Biull Eksp Biol Med. 101:717-9.

Gotoh Y, Hiraiwa K, Nagayama M. 1990 In vitro mineralization of osteoblastic cells derived from human bone. Bone Miner. 8:239-50.

Hamaguchi I, Huang X L, Takakura N, Tada J, Yamaguchi Y, Kodama H, Suda T. 1999 In vitro hematopoietic and endothelial cell development from cells expressing TEK receptor in murine aorta-gonad-mesonephros region. Blood. 93:1549-56.

He Z, Huang S, Li Y, Zhang Q. 2002 Human embryonic stem cell lines preliminarily established in China. Zhonghua Yi Xue Za Mi. 82:1314-8.

Hofmann G O, Kirschner M H, Gonschorek O, Buhren V. 1998 Bridging long bone and joint defects with allogeneic vascularized transplants. Langenbecks Arch Chir Suppl Kongressbd. 115:1285-7.

Horwitz E M, Prockop D J, Fitzpatrick L A, Koo W W, Gordon P L, Neel M, Sussman M, Orchard P, Marx J C, Pyeritz R E, Brenner M K. 1999 Transplantability and therapeutic effects of bone marrow-derived mesenchymal cells in children with osteogenesis imperfecta. Nat Med. 5:309-13.

Horwitz E M, Prockop D J, Gordon P L, Koo W W, Fitzpatrick L A, Neel M D, McCarville M E, Orchard P J, Pyeritz R E, Brenner M K. 2001 Clinical responses to bone marrow transplantation in children with severe osteogenesis imperfecta. Blood. 97:1227-31.

Horwitz E M, Gordon P L, Koo W K, Marx J C, Neel M D, McNall R Y, Muul L, Hofmann T. 2002 Isolated allogeneic bone marrow-derived mesenchymal cells engraft and stimulate growth in children with osteogenesis imperfecta: Implications for cell therapy of bone. Proc Natl Acad Sci USA. 99:8932-7.

Hovatta O, Mikkola M, Gertow K, Stromberg A M, Inzunza J, Hreinsson J, Rozell B, Blennow E, Andang M, Ahrlund-Richter L. 2003 A culture system using human foreskin fibroblasts as feeder cells allows production of human embryonic stem cells. Hum Reprod. 18:1404-9.

Jaiswal N, Haynesworth S E, Caplan A I, Bruder S R 1997 Osteogenic differentiation of purified, culture-expanded human mesenchymal stem cells in vitro. J Cell Biochem. 64:295-312.

Johnson D R. 2000 Differential expression of human major histocompatibility class I loci: HLA-A, -B, and -C. Hum Immunol. 61:389-96.

Kadiyala S, Young R G, Thiede M A, Bruder S R 1997 Culture expanded canine mesenchymal stem cells possess osteochondrogenic potential in vivo and in vitro. Cell Transplant. 6:125-34.

Kawaguchi H, Hirachi A, Hasegawa N, Iwata T, Hamaguchi H, Shiba H, Takata T, Kato Y, Kurihara H. 2004 Enhancement of periodontal tissue regeneration by transplantation of bone marrow mesenchymal stem cells. J Periodontol. 75:1281-7.

Koc O N, Peters C, Aubourg P, Raghavan S, Dyhouse S, DeGasperi R, Kolodny E H, Yoseph Y B, Gerson S L, Lazarus H M, Caplan A I, Watkins P A, Krivit W. 1999 Bone marrow-derived mesenchymal stem cells remain host-derived despite successful hematopoietic engraftment after allogeneic transplantation in patients with lysosomal and peroxisomal storage diseases. Exp Hematol. 27:1675-81.

Krampera M, Glennie S, Dyson J, Scott D, Laylor R, Simpson E, Dazzi F. 2003 Bone marrow mesenchymal stem cells inhibit the response of naive and memory antigen-specific T cells to their cognate peptide. Blood. 101:3722-9.

Lane J M, Yasko A W, Tomin E, Cole B J, Waller S, Browne M, Turek T, Gross J. 1999 Bone marrow and recombinant human bone morphogenetic protein-2 in osseous repair. Clin Orthop. 361:216-27.

Lee O K, Kuo T K, Chen W M, Lee K D, Hsieh S L, Chen T H. 2004 Isolation of multipotent mesenchymal stem cells from umbilical cord blood. Blood. 103:1669-75.

Lee W Y, Cho S W, Oh E S, Oh K W, Lee J M, Yoon K H, Kang M I, Cha B Y, Lee K W, Son H Y, Kang S K, Kim C C. 2002 The effect of bone marrow transplantation on the osteoblastic differentiation of human bone marrow stromal cells. J Clin Endocrinol Metab. 87:329-35.

Lewandrowski K U, Gresser J D, Wise D L, Trantol D J. 2000 Bioresorbable bone graft substitutes of different osteoconductivities: a histologic evaluation of osteointegration of poly(propylene glycol-co-fumaric acid)-based cement implants in rats. Biomaterials. 21:757-64.

Maitra B, Szekely E, Gjini K, Laughlin M J, Dennis J, Haynesworth S E, Koc O N. 2004 Human mesenchymal stem cells support unrelated donor hematopoietic stem cells and suppress T-cell activation. Bone Marrow Transplant. 33:597-604.

Mitchell K E, Weiss M L, Mitchell B M, Martin P, Davis D, Morales L, Helwig B, Beerenstrauch M, Abou-Easa K, Hildreth T, Troyer D, Medicetty S. 2003 Matrix cells from Wharton's jelly form neurons and glia. Stem Cells. 21:50-60.

Mizuno H, Hyakusoku H. 2003 Mesengic potential and future clinical perspective of human processed lipoaspirate cells. J Nippon Med Sch. 70:300-6.

Murohara T, Ikeda H, Duan J, Shintani S, Sasaki K, Eguchi H, Onitsuka I, Matsui K, Imaizumi T. 2000 Transplanted cord blood-derived endothelial precursor cells augment postnatal neovascularization. J Clin Invest. 105:1527-36.

Nade S, Armstrong L, McCartney E, Baggaley B. 1983 Osteogenesis after bone and bone marrow transplantation. The ability of ceramic materials to sustain osteogenesis from transplanted bone marrow cells: preliminary studies. Clin Orthop Relat Res. 181:255-63.

Neppert J, Nunez G, Stastny P. 1984 HLA-A, B, C; -DR; -MT, -MB, and SB antigens on unstimulated human endothelial cells. Tissue Antigens. 24:40-7.

Nilsson S K, Dooner M S, Weier H U, Frenkel B, Lian J B, Stein G S, Quesenberry P J. 1999 Cells capable of bone production engraft from whole bone marrow transplants in nonablated mice. J Exp Med. 189:729-34.

Niemeyer P, Seckinger A, Simank H G, Kasten P, Sudkamp N, Krause U. 2004 Allogenic transplantation of human mesenchymal stem cells for tissue engineering purposes: an in vitro study. Orthopade. 33:1346-53.

Ohgushi H, Okumura M, Tamai S, Shors E C, Caplan A L 1990 Marrow cell induced osteogenesis in porous hydroxyapatite and tricalcium phosphate: a comparative histomorphometric study of ectopic bone formation. J Biomed Mater Res. 24:1563-70.

Pereira R F, Halford K W, O'Hara M D, Leeper D B, Sokolov B P, Pollard M D, Bagasra O, Prockop D J. 1995 Cultured adherent cells from marrow can serve as long-lasting precursor cells for bone, cartilage, and lung in irradiated mice. Proc Natl Acad Sci USA. 92:4857-61.

Petersen B E, Bowen W C, Patrene K D, Mars W M, Sullivan A K, Murase N, Boggs S S, Greenberger J S, Goff J R 1999 Bone marrow as a potential source of hepatic oval cells. Science. 284:1168-70.

Ringe J, Kaps C, Schmitt B, Buscher K, Bartel J, Smolian H, Schultz O, Burmester G R, Haupl T, Sittinger M. 2002 Porcine mesenchymal stem cells. Induction of distinct mesenchymal cell lineages. Cell Tissue Res. 307:321-7.

Schmidt G M, Horak D A, Niland J C, Duncan S R, Forman S J, Zaia J A. 1991 A randomized, controlled trial of prophylactic ganciclovir for cytomegalovirus pulmonary infection in recipients of allogeneic bone marrow transplants; The City of Hope-Stanford-Syntex CMV Study Group. N Engl J Med. 1991 324:1005-11.

Shahgasempour S, Woodroffe S B, Garnett H M. 1998 Modulation of HLA class I antigen and ICAM-2 on endothelial cells after in vitro infection with human cytomegalovirus. Immunol Cell Biol. 76:217-21

Shang Q, Wang Z, Liu W, Shi Y, Cui L, Cao Y. 2001 Tissue-engineered bone repair of sheep cranial defects with autologous bone marrow stromal cells. J Craniofac Surg. 12:586-93;

Sottile V, Thomson A, McWhir J. 2003 In vitro osteogenic differentiation of human ES cells. Cloning Stem Cells. 5:149-55.

Sun S, Guo Z, Xiao X, Liu B, Liu X, Tang P H, Mao N. 2003 Isolation of mouse marrow mesenchymal progenitors by a novel and reliable method. Stem Cells. 21:527-35.

Suparno C, Milligan D W, Moss P A, Mautner V. 2004 Adenovirus infections in stem cell transplant recipients: recent developments in understanding of pathogenesis, diagnosis and management. Leuk Lymphoma. 45:873-85.

Theunissen K, Verfaillie C M. 2005 A multifactorial analysis of umbilical cord blood, adult bone marrow and mobilized peripheral blood progenitors using the improved ML-IC assay. Exp Hematol. 33:165-72.

Valimaki M J, Kinnunen K, Volin L, Tahtela R, Loyttyniemi E, Laitinen K, Makela P, Keto P, Ruutu T. 1999 A prospective study of bone loss and turnover after allogeneic bone marrow transplantation: effect of calcium supplementation with or without calcitonin. Bone Marrow Transplant. 23:355-61.

Wakitani S, Takaoka K, Hattori T, Miyazawa N, Iwanaga T, Takeda S, Watanabe T K, Tanigami A. 2003 Embryonic stem cells injected into the mouse knee joint form teratomas and subsequently destroy the joint. Rheumatology (Oxford). 42:162-5.

Wang H S, Hung S C, Peng S T, Huang C C, Wei H M, Guo Y J, Fu Y S, Lai M C, Chen C C. 2004 Mesenchymal stem cells in the Wharton's jelly of the human umbilical cord. Stem Cells. 22:1330-7.

Werntz J R, Lane J M, Burstein A H, Justin R, Klein R, Tomin E. 1996 Qualitative and quantitative analysis of orthotopic bone regeneration by marrow. J Orthop Res. 14:85-93.

Winston D J, Ho W G, Champlin R E. 1990 Cytomegalovirus infections after allogeneic bone marrow transplantation. Rev Infect Dis. 12 Suppl 7:S776-92.

Yoshikawa T, Ohgushi H. 1999 Autogenous cultured bone graft-bone reconstruction using tissue engineering approach. Ann Chir Gynaecol. 88:186-92.

Zuk P A, Zhu M, Mizuno H, Huang J, Futrell J W, Katz A J, Benhaim P, Lorenz H P, Hedrick M H. 2001 Multilineage cells from human adipose tissue: implications for cell-based therapies. Tissue Eng. 7:211-28.

Zuk P A, Zhu M, Ashjian P, De Ugarte D A, Huang J I, Mizuno H, Alfonso Z C, Fraser J K, Benhaim P, Hedrick M H. 2002 Human adipose tissue is a source of multipotent stem cells. Mol Biol Cell. 13:4279-95.

zur Nieden N I, Kempka G, Ahr H J. 2003 In vitro differentiation of embryonic stem cells into mineralized osteoblasts. Differentiation. 71:18-27.

What is claimed is:

1. A mineral implant having a biocompatible, pre-shaped, three-dimensional mineral scaffold comprising ex vivo expanded mesenchymal cells and at least one cell type selected from the group consisting of: osteoblasts, osteoclasts, chondrocytes, endothelial cells and progenitors thereof, wherein said mesenchymal cells and said at least one cell type are organized in more than one layer in a 3-D interaction, wherein said mesenchymal cells comprise a combination of osteoprogenitor cells and mesenchymal stem cells, wherein said mesenchymal cells and at least one cell type are at a density of at least $10^6$ cells/ml in said implant, wherein said pre-shaped is adapted for insertion into a bone lesion.

2. The implant claim 1, wherein said scaffold comprises a bone particle selected from the group consisting of: a dry bone particle, a frozen bone particle and a dematerialized bone particle.

3. The implant claim 1, wherein said scaffold comprises a material selected from the group consisting of: calcium phosphate derivatives, calcium sulfate derivatives, calcium hydroxyapatite, silicate matrices, hydroxyapatite, and beta-3 calcium phosphate.

4. The implant claim 1, wherein said scaffold comprises a pore size in the range of 50 microns to 2000 microns.

5. The implant claim 1, wherein said scaffold comprises a coating layer.

6. The implant claim 5, wherein said coating layer comprises a material selected from the group consisting of: poly-D-lysine, collagen, fibronectin ECM and hydrogel, or a combination thereof.

7. The implant claim 1, wherein said scaffold is pre-shaped to be fitted into a bone lesion.

8. The implant claim 1, wherein said mesenchymal cells and at least one cell type selected from the group consisting of: osteoblasts, osteoclasts, chondrocytes, endothelial cells and progenitors thereof were exposed to shear forces.

9. A method of producing a mineral implant in accordance with claim 1, comprising isolating, expanding and co-cultivating mesenchymal cells and at least one cell type selected from the group consisting of osteoblasts, osteoclasts, chondrocytes, endothelial cells and progenitors thereof on a biocompatible, pre-shaped, three-dimensional scaffold, wherein said mesenchymal cells and said at least one cell type are organized in more than one layer in a three-dimensional interaction, wherein said mesenchymal cells comprise a combination of osteoprogenitor cells and mesenchymal stem cells, wherein said mesenchymal cells and at least one cell type are at a density of at least $10^6$ cells/ml in said implant, wherein said pre-shaped is adapted for insertion into a bone lesion.

10. The method of claim 9, wherein said method is performed in a bioreactor.

11. The method of claim 9, wherein said at least one cell type is obtained from a source selected from the group consisting of an autologous source, a syngeneic source, and an allogeneic source, or a combination thereof.

12. The method of claim 11, wherein said source is selected from the group consisting of bone marrow, placenta, adipose tissue, cord blood, cord vein, peripheral blood, mobilized peripheral blood, and embryonic stem cells.

13. The method of claim 2, wherein said three-dimensional scaffold has a pore size in the range of about 50 microns to about 2000 microns.

14. The method of claim 9, wherein said three-dimensional scaffold comprises a coating layer.

15. The method of claim 14, wherein said coating layer comprises a material selected from the group consisting of poly-D-lysine, collagen, fibronectin, ECM and hydrogel, or a combination thereof.

16. The method of claim 9, wherein said mesenchymal cells and at least one cell type are isolated from bone marrow, fat tissue, placenta or cord vein.

17. The method of claim 9, wherein said co-cultivation comprises subjecting said cells to an osteogenic stimulus.

18. The method of claim 17, wherein said step of subjecting said cells to an osteogenic stimulus comprises contacting the cells with a molecule selected from the group consisting of dexamethasone, sodium B-glycerophosphate, 1,25 dihydroxycholecalciferol calcitriol and, L-ascorbic acid-2-phosphate.

* * * * *